(12) United States Patent
Sarussi et al.

(10) Patent No.: US 7,590,438 B2
(45) Date of Patent: *Sep. 15, 2009

(54) PHYSIOLOGICAL STRESS DETECTOR DEVICE AND SYSTEM

(75) Inventors: Israel Sarussi, D.N. Hof Aza (IL); Yehuda Heimenrath, Neve Dekalim (IL)

(73) Assignee: SPO Medical Equipment Ltd., Kfar Saba (IL)

( * ) Notice: Subject to any disclaimer, the term of this patent is extended or adjusted under 35 U.S.C. 154(b) by 335 days.

This patent is subject to a terminal disclaimer.

(21) Appl. No.: 11/567,230

(22) Filed: Dec. 6, 2006

(65) Prior Publication Data

US 2007/0149871 A1 Jun. 28, 2007

Related U.S. Application Data

(63) Continuation of application No. 10/390,169, filed on Mar. 18, 2003, now Pat. No. 7,171,251, which is a continuation-in-part of application No. 09/147,683, filed on Feb. 1, 2000, now Pat. No. 6,553,242.

(51) Int. Cl.
*A61B 5/1455* (2006.01)
*A61B 5/02* (2006.01)

(52) U.S. Cl. ................ 600/324; 600/330; 600/502

(58) Field of Classification Search ............... 600/322, 600/323, 330, 336, 324, 502
See application file for complete search history.

(56) References Cited

U.S. PATENT DOCUMENTS

| | | | | | |
|---|---|---|---|---|---|
| 4,086,915 | A | * | 5/1978 | Kofsky et al. | ............... 600/330 |
| 4,266,554 | A | * | 5/1981 | Hamaguri | ............... 600/323 |
| 4,824,242 | A | * | 4/1989 | Frick et al. | ............... 600/330 |
| 5,351,685 | A | * | 10/1994 | Potratz | ............... 600/330 |
| 5,431,170 | A | * | 7/1995 | Mathews | ............... 600/323 |
| 6,553,242 | B1 | * | 4/2003 | Sarussi | ............... 600/330 |

* cited by examiner

*Primary Examiner*—Eric F Winakur
(74) *Attorney, Agent, or Firm*—Daniel J. Swirsky; AlphaPatent Associates Ltd.

(57) ABSTRACT

A method, system and device for measurement of a blood constituent level, including a light source, a light detector proximate an organ surface, adjustable gain amplifiers, and a processor/controller connected within a processing unit operative to separate AC and DC signal components. The device may determine the level of blood constituent, may use this level for monitoring and/or to activate an alarm when the level falls outside a predetermined range, may be applied to monitoring conditions of apnea, respiratory stress, and reduced blood flow in organ regions, heart rate, jaundice, and blood flow velocity, and may be incorporated within a monitoring system.

14 Claims, 16 Drawing Sheets

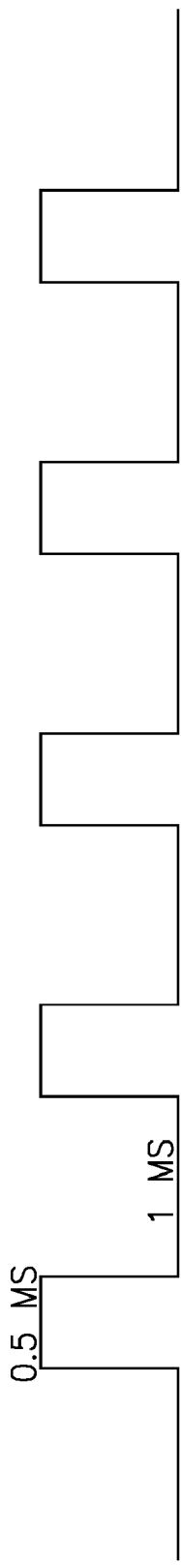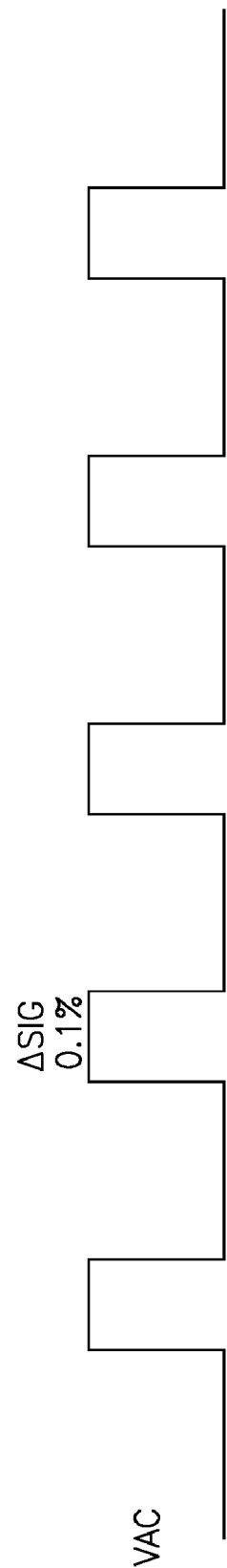

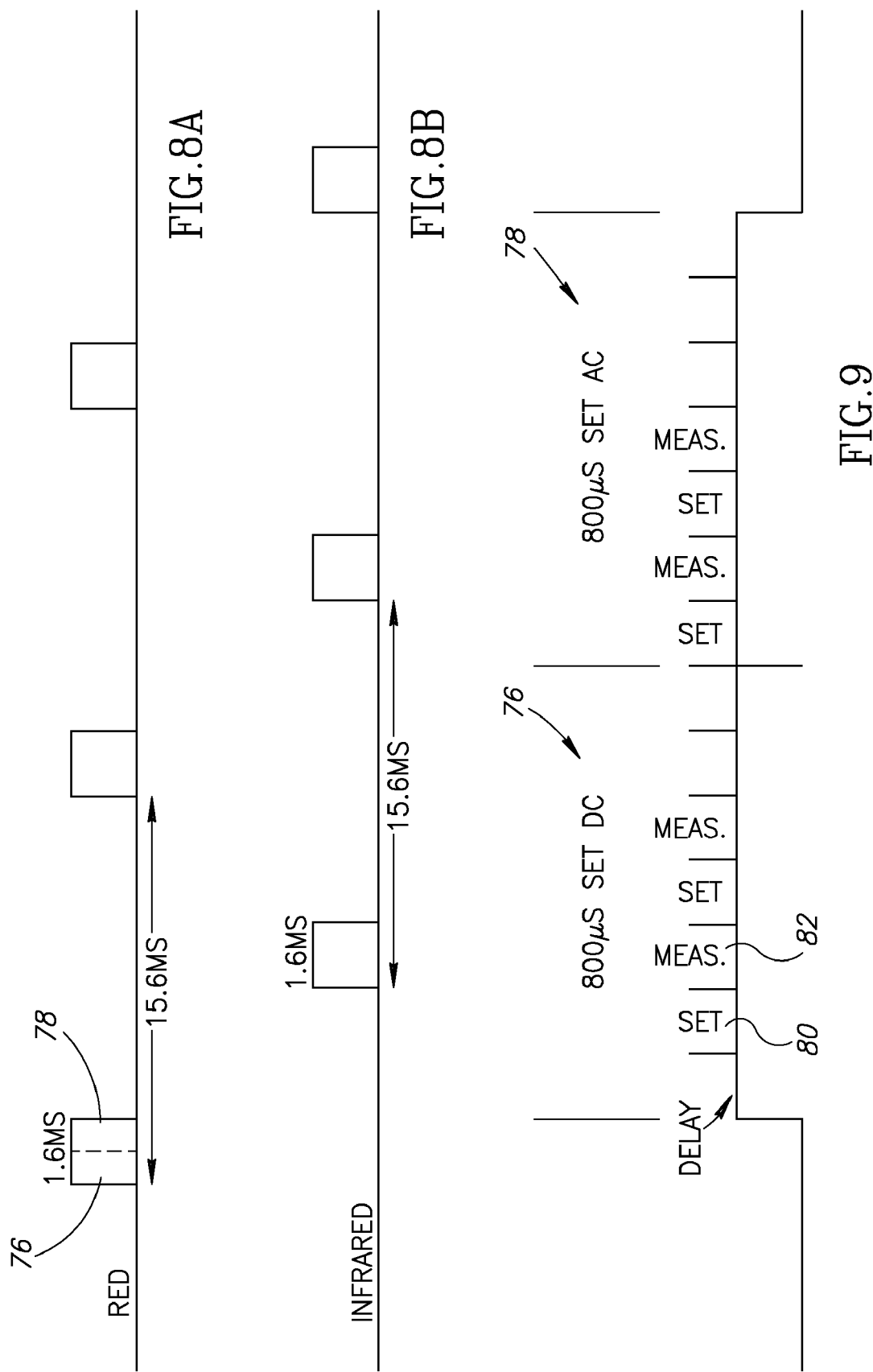

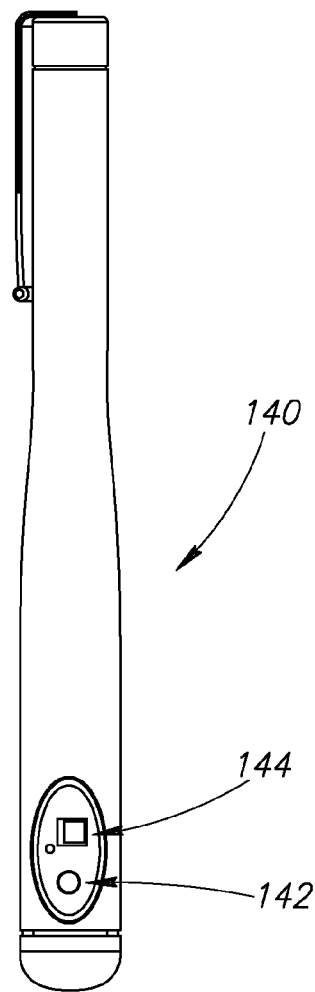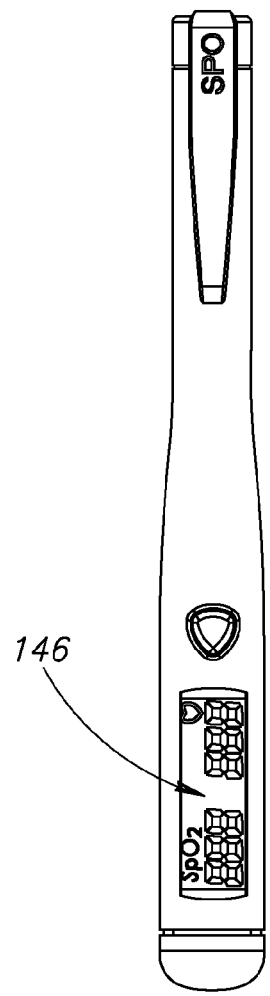
FIG.14A          FIG.14B
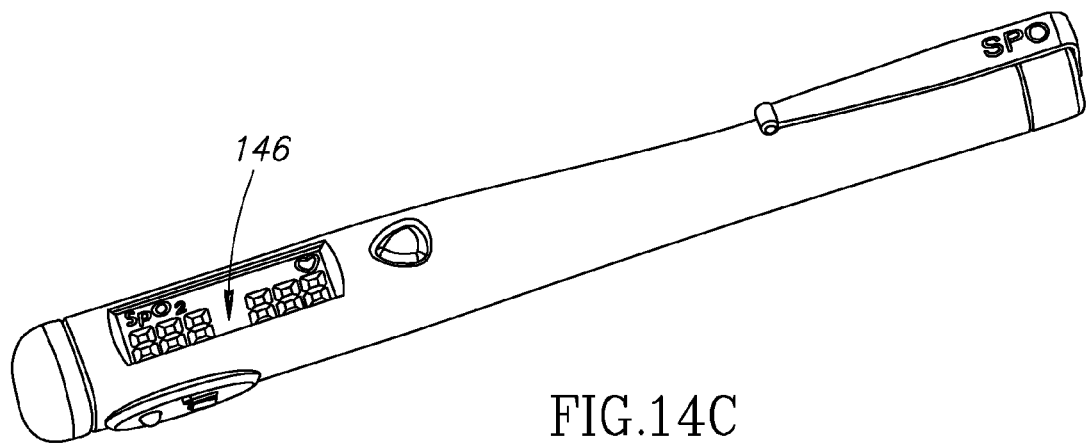
FIG.14C

PHYSIOLOGICAL STRESS DETECTOR DEVICE AND SYSTEM

CROSS-REFERENCE TO RELATED APPLICATIONS

This application is a continuation of U.S. patent application Ser. No. 10/390,169, filed Mar. 18, 2003, entitled "Physiological stress detector device and system," now U.S. Pat. No. 7,171,251, which is a continuation-in-part application of U.S. patent application Ser. No. 09/147,683, filed Feb. 1, 2000, entitled "Physiological stress detector device and system," now U.S. Pat. No. 6,553,242, both of which are incorporated herein by reference in their entirety.

FIELD OF THE INVENTION

The present invention relates to instruments that operate on the principle of pulse oximetry, in particular, to non-invasive hemoglobin saturation detectors and methods, and may be generally applied to other electro-optical methods of measuring blood constituents.

BACKGROUND OF THE INVENTION

Electro-optical measurement of blood characteristics has been found to be useful in many areas of blood constituent diagnostics, such as glucose levels, oxygen saturation, hematocrit, billirubin and others. This method is advantageous in that it can be performed in a non-invasive fashion. In particular, much research has been done on oximetry, a way of measuring oxygen saturation in the blood, as an early indicator of respiratory distress.

Infants during the first year of life are susceptible to breathing disturbances (apnea) and respiratory distress. Sudden Infant Death Syndrome (SIDS) is a medical condition in which an infant enters respiratory distress and stops breathing, leading to the death of the infant. Although the cause and warning signs of SIDS are not clear, it has been shown that early detection of respiratory distress can provide the time to administer the aid necessary to prevent death.

Many types of baby monitors are currently available, from simple motion detectors to complicated systems which stream oxygen enriched air into the infant's environment. Some of the more accepted monitoring methods include chest motion monitors, carbon dioxide level monitors and heart rate (pulse) monitors. Unfortunately these methods often do not give the advance warning necessary for the caregivers to administer aid. In addition, these monitors are administered by attaching a series of straps and cords, which are cumbersome to use and present a strangulation risk.

The chest motion monitor gives no warning when the breathing patterns become irregular or when hyperventilation is occurring, since the chest continues to move. Distress is only noted once the chest motion has ceased at which point there may only be a slight chance of resuscitation without brain damage. In addition these devices are known to have a high level of "false alarms" as they have no way to distinguish between the lapses in breathing which are normal for an infant (up to 20 seconds) and respiratory distress. These devices can cause excessive anxiety for the caregivers or cause them to ignore a signal, which is true after responding repeatedly to false alarms.

Among other symptoms, SIDS causes an irregular heartbeat, resulting eventually in the cessation of heartbeat with the death of the infant. There are some instruments, which use the EKG principle to monitor this clinical phenomenon. This is a limited method that has a very high rate of false positives since the monitors have inadequate algorithms to determine what is a SIDS event. Obviously, this is not a convenient method, nor is it desirable to have the infant constantly hooked up to an EKG monitor.

In light of these disadvantages a better method to use is a form of electro-optical measurement, such as pulse oximetry, which is a well-developed art. This method uses the difference in the absorption properties of oxyhemoglobin and deoxyhemoglobin to measure blood oxygen saturation in arterial blood. The oximeter passes light, usually red and infrared, through the body tissue and uses a photo detector to sense the absorption of light by the tissue. By measuring oxygen levels in the blood, one is able to detect respiratory distress at its onset giving sufficiently early warning to allow aid to be administered as necessary.

Two types of pulse oximetry are known. Until now, the more commonly used type has been transmission oximetry in which two or more wavelengths of light are transmitted through the tissue at a point where blood perfuses the tissue (i.e. a finger or earlobe) and a photo detector senses the absorption of light from the other side of the appendage. The light sources and sensors are mounted in a clip that attaches to the appendage and delivers data by cable to a processor. These clips are uncomfortable to wear for extended periods of time, as they must be tight enough to exclude external light sources. Additionally, the tightness of the clips can cause hematoma. Use of these clips is limited to the extremities where the geometry of the appendages is such that they can accommodate a clip of this type. The clip must be designed specifically for one appendage and cannot be used on a different one. Children are too active to wear these clips and consequently the accuracy of the reading suffers.

In another form of transmission oximetry, the light source and detector are placed on a ribbon, often made of rubber, which is wrapped around the appendage so that the source is on one side and the detector is on the other. This is commonly used with children. In this method error is high because movement can cause the detector to become misaligned with the light source.

It would be preferable to be able to use the other type of pulse oximetry known as reflective, or backscattering, oximetry, in which the light sources and light detector are placed side by side on the same tissue surface. When the light sources and detector can be placed on the tissue surface without necessitating a clip they can be applied to large surfaces such as the head, wrist or foot. In cases such as shock, when the blood is centralized away from the limbs, this is the way meaningful results can be obtained.

One difficulty in reflective oximetry is in adjusting the separation between the light source and the detector such that the desired variable signal component (AC) received is strong, since it is in the alternating current that information is received. The challenge is to separate the shunted, or coupled, signal which is the direct current (DC) signal component representing infiltration of external light from the AC signal bearing the desired information. This DC signal does not provide powerful information. If the DC signal component is not separated completely, when the AC signal is amplified any remaining DC component will be amplified with it, corrupting the results. Separating out the signal components is not a simple matter since the AC signal component is only 0.1% to 1% of the total reflected light received by the detector. Many complicated solutions to this problem have been proposed.

If the light source and detector are moved further apart, this reduces the shunting problem (DC), however, it also weakens the already weak AC signal component. If the light source and detector are moved close together to increase the signal, the shunting (DC) will overpower the desired signal (AC).

Takatani et al., in U.S. Pat. No. 4,867,557, Hirao et al., in U.S. Pat. No. 5,057,695 and Mannheimer, in U.S. Pat. No: 5,524,617 all disclose reflective oximeters that require multiple emitters or detectors in order to better calculate the signal.

A number of attempts have been made to filter out the DC electronically (see Mendelson et al., in U.S. Pat. No. 5,277, 181). These methods are very sensitive to changes in signal level. The AC remaining after the filtering often contains a small portion of DC, which upon amplification of the AC becomes amplified as well, resulting in inaccurate readings. Therefore, this method is only useful in cases where the signal is strong and uniform.

Israeli patents 114082 and 114080 disclose a sensor designed to overcome the shunting problem by using optical fibers to filter out the undesired light. This is a complicated and expensive solution to the problem that requires a high level of technical skill to produce. In addition, it is ineffectual when the AC signal is relatively weak.

As can be seen from the above discussion, the prior art methods of addressing the AC/DC signal separation problem in reflective oximetry techniques are complicated and expensive. Therefore, it would be desirable to provide a simple, low cost and effective method for achieving accurate reflective or transmitted oximetry detection of respiratory stress.

SUMMARY OF THE INVENTION

Accordingly, it is the broad object of the present invention to overcome the problems of separating the shunted light from the signal in order to provide a physiological stress detector that achieves accurate readings.

A general object of this invention is to overcome the problems of separating the shunted light from the signal in order to provide a respiratory stress detector that achieves accurate pulse oximetry readings for respiratory stress applications.

The present invention discloses a small, independent, sensor, for invasive and non-invasive applications unencumbered by cables or wires, which is capable of being attached to different body parts, to comfortably and accurately monitor blood constituent levels and the pulse of an infant or any other living organism. The apparatus may be applied to any part of the body without prior calibration. Accurate readings of blood constituent levels are obtained using the inventive method in which a precise separation of the AC and DC signal components has been achieved, allowing each signal component to be amplified separately. In order to accomplish this precise separation, the signal components are separated by a novel signal processing technique.

The inventive sensor may be adapted for many health-monitoring situations including infant monitoring for SIDS, fetal monitoring, etc.

In an embodiment adapted for SIDS, the sensor is designed to apply reflective oximetry techniques, so as to comfortably and accurately monitor the arterial oxygen levels and the pulse of an infant or any other living organism prone to respiratory distress. This monitor is equipped with a processor capable of determining the need for an alarm and capable of signaling a distress signal to further alert to a crisis.

In another embodiment, in addition to the alarm being generated from the sensor itself, readings will be radio-transmitted to a base station, possibly at a nurse's station, to allow monitoring of the reading, and another alarm will be activated from the base station when the readings are outside of the accepted range.

In another embodiment, the apparatus is mounted in a sock-type mounting such that the apparatus is properly applied when the sock is put on in the usual fashion. In addition, the sock-type apparatus blocks entrance of external light to the area of the sensor apparatus.

In yet another embodiment, the apparatus is mounted on a ribbon-type mounting such that the apparatus is properly applied when the ribbon is tied around the head or other body part. In addition, the width of the ribbon is such that it will block entrance of external light to the area of the sensor apparatus. Additionally, the ribbon may be of dark color, which also blocks entrance of external light to the area of the sensor apparatus.

In yet another embodiment, the apparatus is mounted on a bracelet-type mounting such that the apparatus is properly applied when the bracelet is fastened to the wrist or other body part. In addition, the width of the bracelet is such that it blocks entrance of external light to the area of the sensor apparatus. Additionally, the bracelet may be of dark color, which also blocks entrance of external light to the area of the sensor apparatus.

There is therefore provided, in accordance with a preferred embodiment of the present invention, a non-invasive device for measurement of blood saturation and heart pulse rate of an organ. The device includes a housing unit having at least one light source, providing light directed toward the surface of the organ, the light being reflected from the organ, a sensor device spaced apart from the light source and being sensitive to intensity levels of the reflected light for producing intensity signals in accordance therewith and a processing unit for processing the intensity signals received from the sensor device and for producing output signals.

Furthermore, in accordance with another preferred embodiment of the present invention, the device further includes a transmitter configured to transmit the output signals to a receiver at a remote location. The device may further include a display unit for displaying the output signals.

Additionally, there is also provided, in accordance with a preferred embodiment of the present invention, a monitoring system which includes a non-invasive device for measurement of blood saturation and heart pulse rate, and a receiver configured to indicate an alert when the blood saturation or heart pulse rate falls outside of a pre-determined range.

The non-invasive device may include a housing unit configured to fit a wrist or ankle, including a baby. The housing unit includes at least one light source, providing light directed toward the surface of the organ, the light being reflected from the organ, a sensor device spaced apart from the light source and being sensitive to intensity levels of the reflected light for producing intensity signals in accordance therewith, a processing unit for processing the intensity signals received from the sensor device and for producing output signals and a transmitter configured to transmit the output signals to a receiver at a remote location. The processing unit may be integrated with the sensor device.

Furthermore, in accordance with another preferred embodiment of the present invention, the display unit may be configured in the shape of a watch. The display unit may include a memory storage unit for storing the output signals. Furthermore, the transmitter may be integrated with the display unit.

Furthermore, in accordance with another preferred embodiment of the present invention, the device further includes an alerter configured to transmit an alert signal. The alerter may be configured to transmit a signal whenever the blood saturation or heart pulse rate falls outside of a pre-determined range.

The alerter may also be configured to transmit data signals including at least the blood saturation or heart pulse rate.

Furthermore, in accordance with another preferred embodiment of the present invention, the housing unit may be configured to be attachable to a head covering, such as a cap, a hat and a bandanna, for example.

Furthermore, in accordance with another preferred embodiment of the present invention, the housing unit may be configured to adhere to the surface of the skin.

Furthermore, in accordance with another preferred embodiment of the present invention, the housing unit may be configured to be integrated within a protective mask, including a search and rescue mask, gas mask, anti biological and chemical mask.

Furthermore, in accordance with another preferred embodiment of the present invention, the device may further include a display or indication unit. The display or indication unit may include an indication of the well being of the wearer.

Furthermore, in accordance with another preferred embodiment of the present invention, the receiving device at the remote location may be a personal digital assistant (PDA).

Furthermore, in accordance with another preferred embodiment of the present invention, the housing unit may be configured to receive a human digit such as a finger.

Furthermore, in accordance with another preferred embodiment of the present invention, the housing unit may be configured in the shape of a pen and the sensor device is located on the external face of the pen, thereby allowing the housing unit to be disposed proximate to the skin.

Furthermore, in accordance with another preferred embodiment of the present invention, the processor develops a control signal when the adjustably-determined second gain amplification factor is established in the second stage, the signal is measured and the control signal shuts off the light source.

Furthermore, in accordance with another preferred embodiment of the present invention, the control signal conserves energy by reducing the operational duty cycle of the light source.

Furthermore, in accordance with another preferred embodiment of the present invention, the first and second gain amplification factors are determined by the processor in an iterative process by adjustably setting a gain amplification factor and measuring a dynamic voltage range of the output signals to determine if the voltage range falls within a predetermined window established by the processor.

Furthermore, in accordance with another preferred embodiment of the present invention, the light source comprises a single light-emitting unit capable of controllably providing light having a wavelength range selected from at least a first wavelength range and a second wavelength range. The first wavelength range is at least partially different from the second wavelength range. The single light-emitting unit can be switched from emitting light within the first wavelength range to emitting light within the second wavelength range.

Furthermore, in accordance with another preferred embodiment of the present invention, the light source includes at least a first light-emitting unit capable of controllably emitting light having a first wavelength range and a second light-emitting unit capable of controllably emitting light having a second wavelength range. The first wavelength range is at least partially different from the second wavelength range.

Furthermore, in accordance with another preferred embodiment of the present invention, the light source provides light having wavelengths in the red and infrared ranges.

Other features and advantages of he invention will become apparent from the following drawings and description.

BRIEF DESCRIPTION OF THE DRAWINGS

For a better understanding, the invention will now be described, by way of example only, with reference to the accompanying drawings in which like numerals designate like components throughout the application, and in which:

FIGS. 3*a*-3*b* show, respectively, a prior art signal waveform representing emitted and received light;

FIGS. 8*a*-*b* are, respectively, signal waveforms representing emitted red and infrared light used in the device of FIG. 1;

FIG. 9 is a timing diagram applied in an automatic gain adjustment procedure during signal processing;

FIGS. 14*a*-14*c* are schematic illustrations of an exemplary application of a device for determining blood saturation and heart pulse rate according to another embodiment of the invention;

DETAILED DESCRIPTION OF PREFERRED EMBODIMENTS

The following description presents a detailed construction of a physiological stress detector device adapted for use in monitoring arterial oxygen levels. In this particular application, the reflective oximetry method uses light wavelengths in the red and infrared ranges, since these are most suitable for detecting oxygen saturation in hemoglobin. As will be understood by those skilled in the art, particular design features used for this application can be varied for different applications. For example, in an application for monitoring jaundice through billirubin levels, other suitable, light wavelengths would be used. Therefore, the light wavelengths discussed in the following description are not intended to limit the scope of the present invention, and are to be understood as pertaining to the subject example only.

Figure 1:
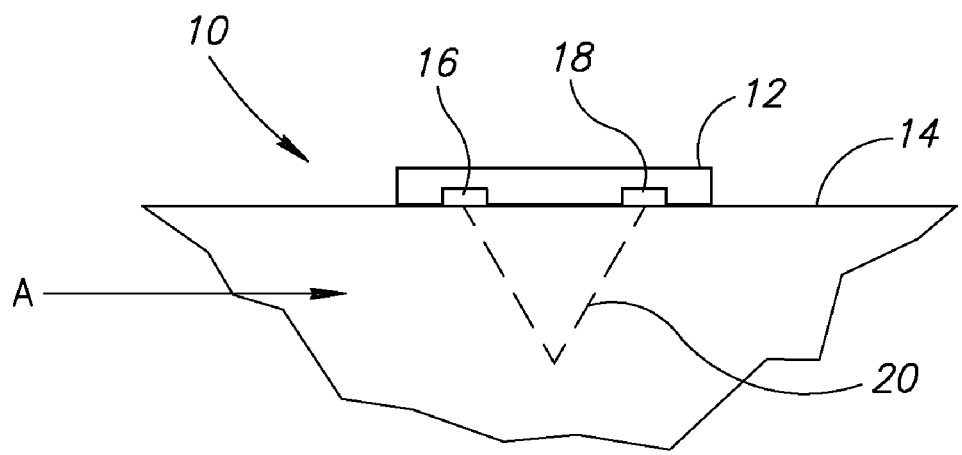
FIG. 1 is a schematic layout diagram of a physiological stress detector device, constructed and operated in accordance with the principles of the present invention.

Referring now to FIG. 1, there is shown a preferred embodiment of a physiological stress detector device 10 constructed and operated in accordance with the principles of the present invention. Device 10 comprises a housing 12 arranged for placement in close proximity to a skin surface 14. Housing 12 may be provided as a casing enclosing a light source 16 emitting two wavelengths, red and infrared, and a photo detector 18 spaced apart from the light source 16. Device 10 is designed to be operated such that when light source 16 emits light of a red or infrared wavelength, the light penetrates skin tissue (arrow A) and a portion of the light is reflected back to light detector 18, along a path defined by line 20.

The light source 16 may be implemented as a single component, which can controllably emits red or infrared light. A non-limiting example of the light source 16 is the selectable wavelength light emitting diode (LED) component model L122R61R880, or for pediatric or prematurely born baby applications the component model SML12R61R880, both components are commercially available from Ledtronics, Calif., U.S.A. However, The light source 16 may also include two separate suitable light sources. For example, the light source 16 may include two separate light sources (not shown) such as an LED emitting red light and another different LED emitting infrared light.

It is noted that, while, preferably, the light source 16 includes one or more LEDs emitting in the suitable red and infrared ranges, other light sources may be used such as incandescent lamps in combination with suitable optical filters, various types of gas discharge or arc lamps, with or without optical filters, diode laser devices, or any other.

For the pulse-oximetry application the light detector 18 may be a photodiode, such as the model BPW34 photodiode, or for pediatric and premature born babies the model BPW34S photodiode, both commercially available from Siemens Semiconductor Group, Germany. However, many other types of photo-detecting devices may be used such as resistive photocells, or any other type of photo detector, which has the required sensitivity at the wavelengths, used for the specific application of the device 10.

Figure 6:
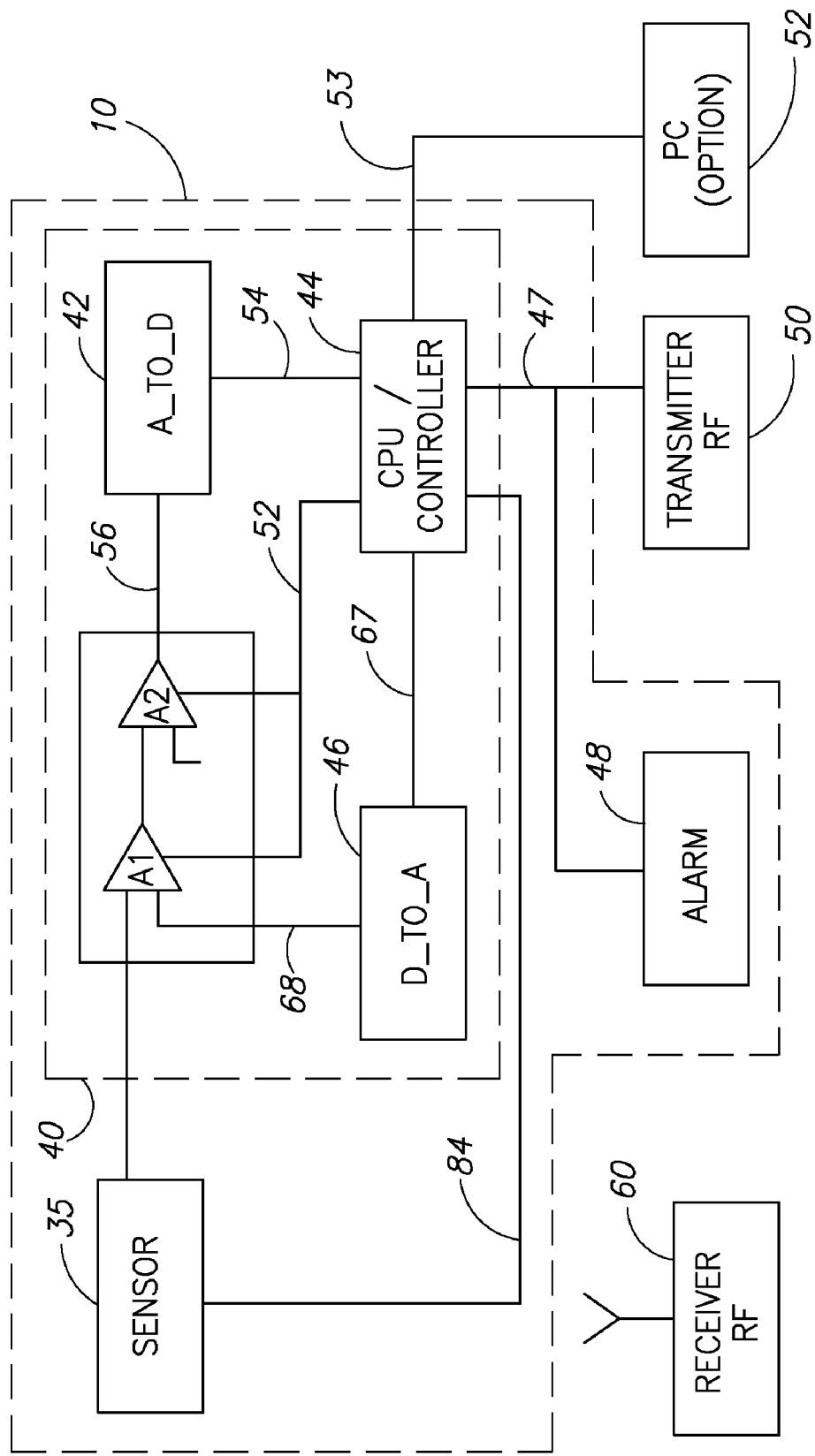
FIG. 6 is an electronic block diagram showing the signal processing components of the device of the present invention.

It is noted that the device 10 of FIG. 1 also includes further electronic components (not shown in FIG. 1), which are disclosed in detail hereinbelow (as best seen in FIG. 6).

Figure 2:
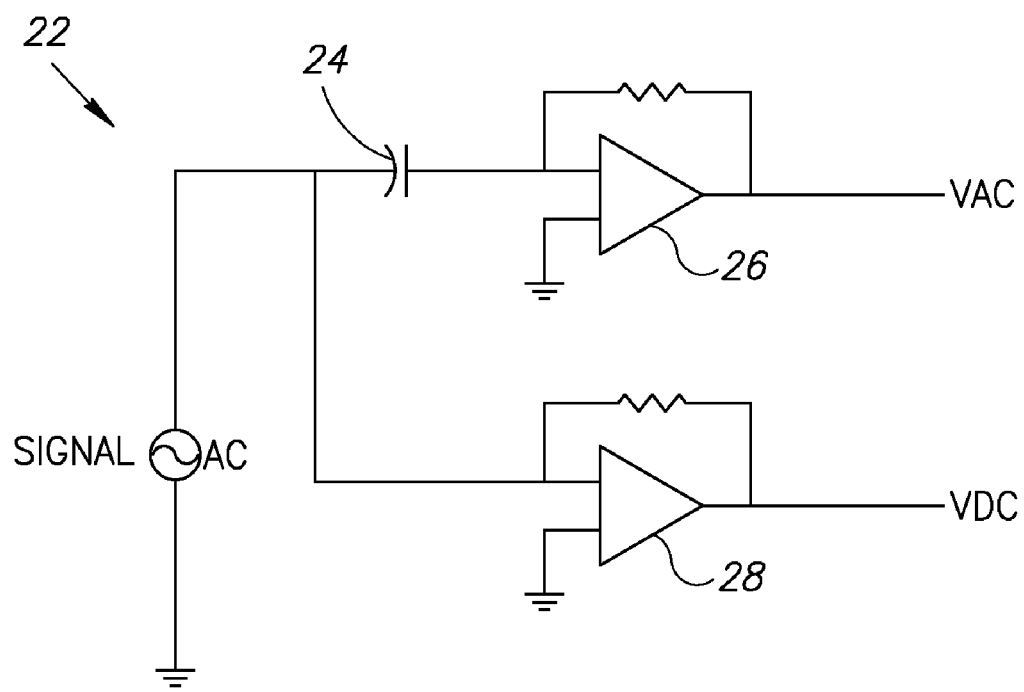
FIG. 2 is an electronic schematic diagram of a prior art signal processing technique, for use with the device of FIG. 1.

As described in the background of the invention, the device 10 employs non-invasive reflective oximetry techniques to provide measurement of blood characteristics useful in diagnostic procedures and detection of physiological stress. As mentioned, one difficulty in reflective oximetry is in adjusting the separation between light source 16 and detector 18 such that the desired signal received by light detector 18 is strong and not affected by shunted, or coupled, light from source 16. FIGS. 2 and 3a-3b illustrate this problem and the prior art techniques currently available for its solution.

In FIG. 2 there is shown an electronic schematic diagram of a signal processing filter 22 used to separate the variable signal (AC) component of received light from the shunted (DC), or coupled, light. The separation is achieved by a blocking capacitor 24 on the input of an operational amplifier 26 used to amplify the variable signal portion. The DC signal component of the received light, which does not pass through blocking capacitor 24, forms the input of, and is amplified by operational amplifier 28.

As illustrated in FIGS. 3a-3b, the signal waveform representing the emitted light, (FIG. 3a) is substantially reproduced as a received signal waveform (FIG. 3b). Even after filtering by signal processing filter 22, the AC signal component remaining ΔSIG is only a small portion of a larger signal, which has been amplified by operational amplifier 26, and therefore dominates the variable signal portion. Thus, this method of signal separation results in inaccurate readings of reflected light, and cannot provide accurate information in oximetry measurements.

Figure 4:
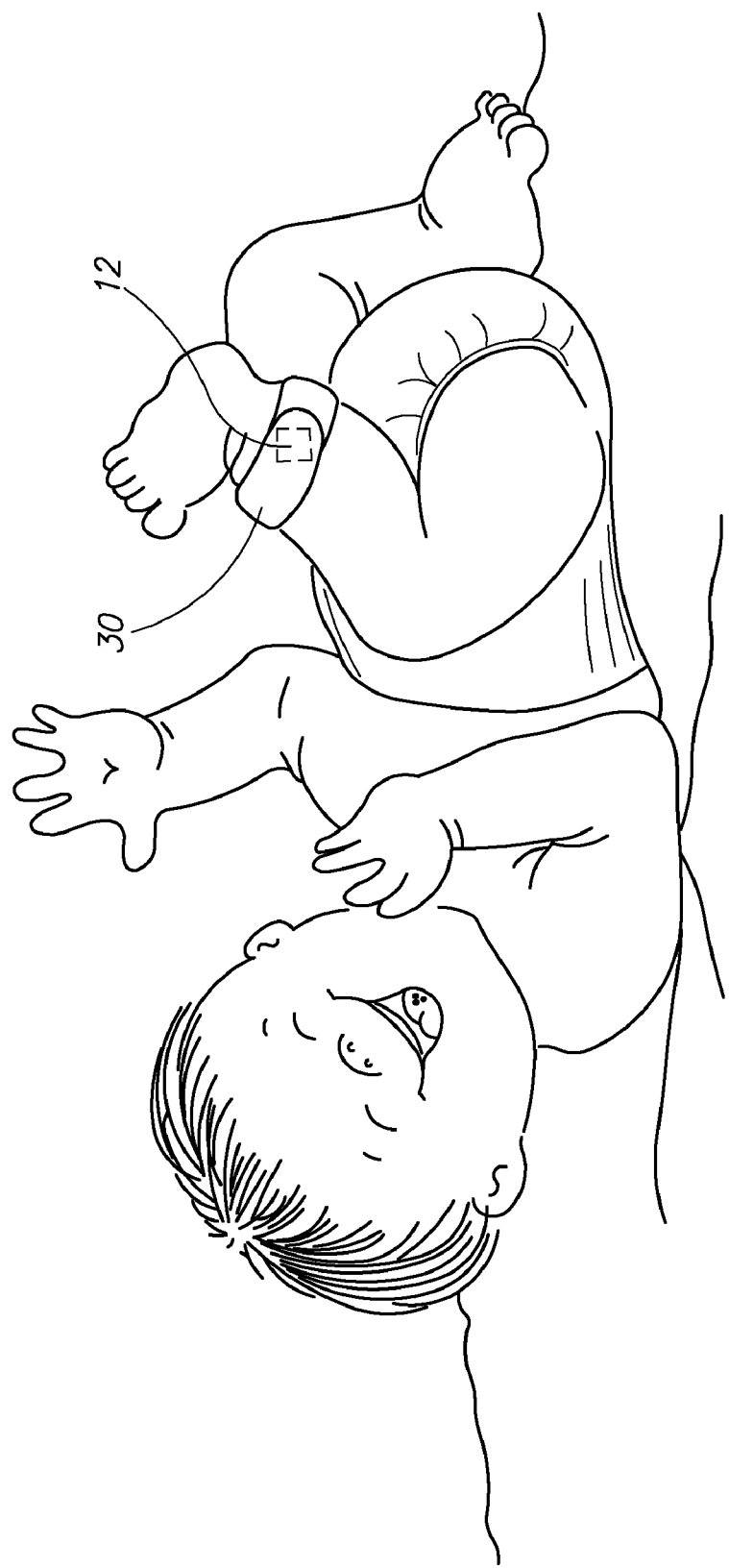
FIGS. 4 and 5*a*-*b* show, respectively, arrangements for wearing the device of FIG. 1 on the body of an infant on a leg, foot or head.
Figure 5B:
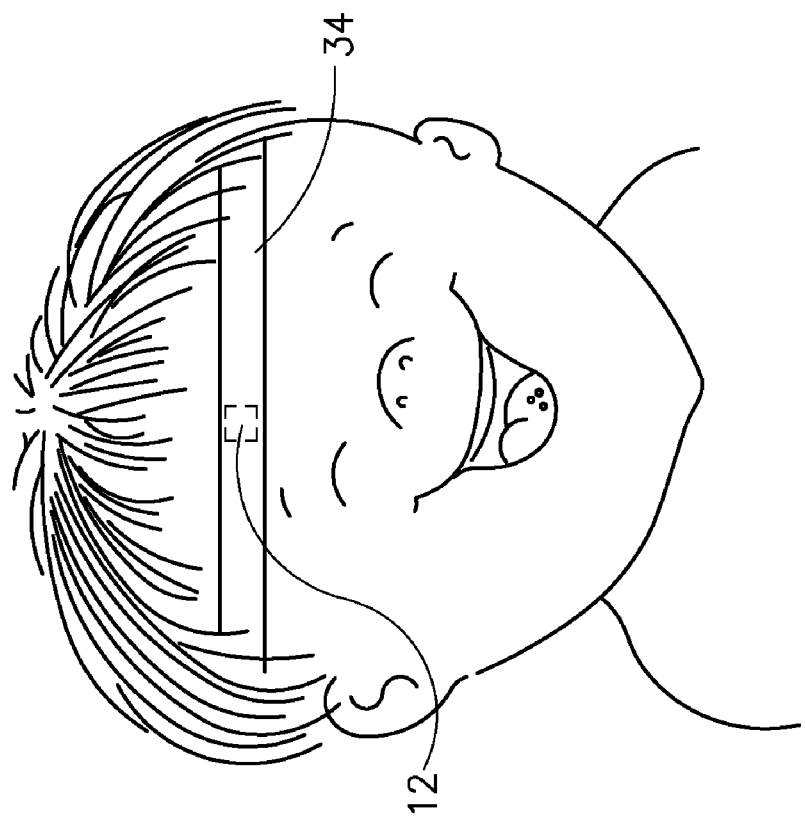
Figure 5A:
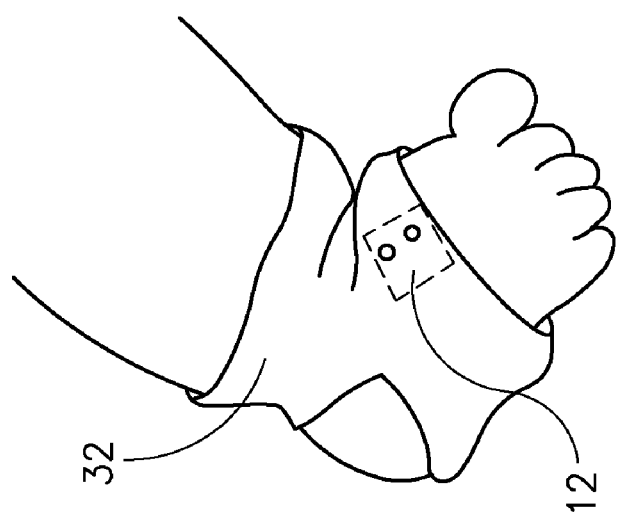

In FIGS. 4 and 5a-b there are shown alternative configurations of device 10, respectively, provided in a foot bracelet 30, a sock 32 worn around the ankle, and a ribbon 34 worn around the head. In each arrangement, casing 12 is designed to be held tightly against skin surface 14 to reduce the amount of stray light entering into the optical path between light source 16 and detector 18.

Preferably, the casing 12 is made from a material opaque to light in the relevant spectral range to which the detector 18 is sensitive, such as an opaque plastic material, metal or the like. The foot bracelet 30, the sock 32 and the ribbon 34 may be made of a material, which allows the casing 12 to be tightly pressed against the skin. This material may be a flexible material such as a flexible fabric. The material may also be a porous or woven material to prevent excessive perspiration of the skin thereunder.

Referring now to FIG. 6, there is shown an electronic schematic block diagram of device 10. Device 10 comprises a sensor 35 incorporating light source 16 and detector 18. The sensor 35 may also include a preamplifier circuit (not shown) for amplifying the output signals of the detector 18 and feeding the amplified signals to the processing unit 40. It will be appreciated by those skilled in the art that the numbers of light sources and detectors can be varied while keeping the same processing method. In addition, device 10 comprises a signal processing unit 40 including a pair of operational amplifiers A1 and A2, an analog to digital converter 42, a central processing unit (CPU)/controller 44, and a digital to analog converter 46. In critical applications, such as SIDS, when there exists a need for emergency first aid availability, when CPU 44 has determined that the value obtained is not within the acceptable range an output signal 47 is fed to an alarm unit 48 causing an alarm to be activated. Optional connections to an RF transmitter 50 and PC computer 52 are available. Sensor 35 is designed to be powered by a small battery (not shown).

According to another embodiment of the present invention, processing unit 40 with or without alarm 48, RF transmitter 50 and/or PC 52 are connected to the sensor 35 via a cable or by wireless transition. In this case sensor 35 does not require a battery.

It is noted that, the alarm unit 48 may activate a visual alarm, an audio alarm, a tactile alarm (such as a vibratory signal), or an audio-visual alarm. The alarm unit 48 may also initiate the automatic dialing of a telephone number and may also activate any combination of any of the above types of alarms, or of other types of alarms.

The coupling of operational amplifiers A1 and A2 is between the output of amplifier A1 and the input of amplifier A2. The gain amplification factor of each amplifier is set by the central processing unit 44 via a signal in accordance with an automatic adjustable gain technique described further herein. Analog to digital converter 42 provides a digital input signal 54 based on the level of output signal 56 from amplifier A2. The central processing unit 44 is programmed to process the information contained in input signal 54, and thereby determine blood oxygen saturation levels detected by sensor 35. The output signal 47 from CPU 44 may be used to trigger alarm 48, or its information can be transmitted by an RF transmitter 50 to a receiver 60 for remote station processing. Data analysis can be performed by PC 52 based on a data output signal 53.

Based on the block diagram of FIG. 6, device 10 can be constructed in accordance with state of the art electronic design techniques employing, for example a 8051 microcontroller, commercially available from Intel Corp, U.S.A., or any other suitable processor or controller to implement the CPU/controller 44.

The properties of amplifiers A1 and A2 are selected in accordance with electronic design rules well known in the art. In a non-limiting example, amplifier A1 is the model PGA205AU programmable gain instrumentation amplifier, and amplifier A2 is the model PGA204AU programmable gain instrumentation amplifier, commercially available from Burr-Brown, Ariz., U.S.A. However, the amplifiers A1 and A2 may be any other suitable type of amplifier. For example, while in the preferred embodiment disclosed hereinabove each of the amplifiers A1 and A2 is shown as an operational amplifier unit, each of the amplifiers A1 and A2 may be implemented as a multi-stage amplifier device containing more than one amplification stages.

As mentioned in the background of the invention, problems with prior art reflective oximetry techniques are related to the measurement of the AC signal component which forms a small part of the larger DC signal component provided by light sensor 35. Whereas the previous techniques involved use of a blocking capacitor 24 as described in FIGS. 2 and 3a-3b, the present invention provides a novel solution to the signal amplification problem such that more accurate oximetry measurement may be obtained.

It is noted that, depending on the specific detector used, the AC and DC signal components generated by the detector 18 may be current or voltage AC and DC signal components, and that the terms AC signal component and DC signal component throughout the specification and claims define AC and DC components of the output signal of the detector 18 and may include voltage signal components and current signal components. However, the AC and DC signal components may also include any other type of electrical or photonic (optical) signal that may be the output of any suitable detector type useful with the device of the present invention.

Figure 7:
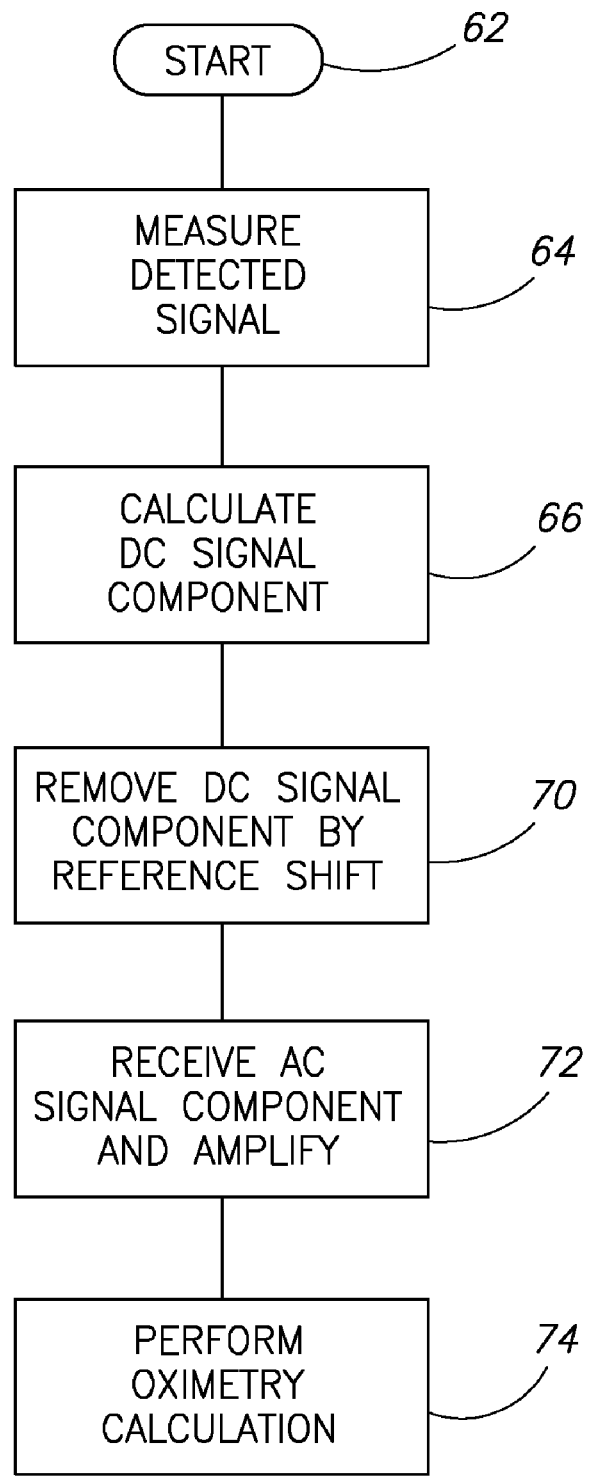
FIG. 7 is an algorithm of a signal processing technique performed in accordance with the principles of the present invention.

In accordance with the principles of the present invention, processing unit 40 applies a novel technique for separating the AC signal component from the DC signal component. The steps carried out by CPU 44 in this technique are illustrated in the flow chart of FIG. 7.

In start block 62, CPU 44 begins its operation by initializing the gain of analog amplifiers A1 and A2 automatically. In block 64 the detected signal from sensor 35 is measured, and this is performed by providing output signal 56 from signal processing unit 40 to the analog to digital converter 42, so that it is converted to a digital input signal 54 for input to CPU 44. In block 66, CPU 44 calculates the DC signal component of the detected signal. A two-stage process achieves this.

In the first stage, output signal 56 is treated as a pure DC signal, such that CPU 44 takes the average of this signal level, and generates a digital output signal 67 which is converted by the digital to analog converter 46 to an analog reference shift signal 68. In block 70, reference shift signal 68 is fed into the negative input of amplifier A1 and amplifier A1 effectively neutralizes the DC component by applying reference shift signal 68 against the detected signal from sensor 35. This produces a null output for input to amplifier A2.

In the second stage, in block 72, amplifier A2 receives the AC signal component of the detected signal and amplifies it, thereby producing an output signal 56 containing information based on the reflective oximetry technique. This information, when converted to a digital signal in analog to digital converter 42, provides digital input signal 54 to CPU 44. In block 74, the oximetry calculation is performed by the CPU/controller 44 based on measurements derived from sensor 35, in accordance with the information provided by digital input signal 54. The results of the oximetry calculation are provided as output signal 47 or in the form of a data signal 35 fed to a PC computer 52. Output signal 47 may be used to activate an alarm 48 or it may be provided as the signal for transmission via RF transmitter 50 to a remote receiver 60, to allow base station monitoring of the reading.

Referring now to FIGS. 8a-b, there are shown respectively, pulse signal waveforms representing light received in the red and infrared ranges by light detector 18 in sensor 35. Light is provided by light source 16 in pulses each having, for example, duration of 1.6 milliseconds and a period of 15.6 milliseconds. The analysis of a typical light pulse is provided in FIG. 9, showing the time scale division of the 1.6 millisecond pulse into two cyclical gain adjustment periods 76 and 78, respectively. The red and infrared pulses are staggered so as to minimize interference between them.

In FIG. 9, a time division scale is developed in which each of the pulsed light waveforms is divided into two periods 76 and 78, each having, for example, a maximum duration of 800 microseconds, during which the gain amplification factor is set for each of operational amplifiers A1 and A2. The first period is used to set the gain for and measure the DC signal component, and the second period is used to set the gain for and measure the AC signal component.

The gain amplification factor is automatically adjusted in an iterative process. After a predetermined delay, for example 50 microseconds, the gain amplification factor is set during interval 80, and the output signal 56 of signal processing unit 40 is measured to determine if it falls within the window defined by CPU 44. For example, a dynamic voltage range of between 0.4-4 volts is established by CPU 44, and output signal 56 is measured during interval 82, to see if it falls within this window. If it does, the gain amplification factor is fixed at its current value. If, on the other hand, output signal 56 does not fall within this window, another setting is provided by CPU 44 and again the output signal 56 is measured. This process is repeated, in iterative fashion, within the first period of the cyclical gain adjustment procedure until the output signal 56 falls within the desired window.

If the desired window for the DC signal component is obtained before the 800 microseconds of the first period has elapsed, the first period is shortened accordingly, and the second period is commenced, during which the same procedure is performed for the AC signal component. Once a desirable window is attained for the AC signal component, the second period may be shortened accordingly, and CPU 44 sends a control signal 84 to sensor 35, to shut off the light source for that pulse. In this fashion, an energy savings is achieved by reducing the duty cycle of light source 16, and reducing the current drain from the battery and extending its useful life. Control signal 84 is provided for each individual light pulse, so that the maximum energy savings is achieved. If the 800 microseconds have elapsed without establishing the gain amplification factor, the signal is ignored.

It is noted that, the values disclosed hereinabove for the pulse duration and pulse interval of FIGS. 8a and 8b and for the two periods 76 and 78 of FIG. 9 are given as a non-limiting example only and may be replaced by other suitable values depending, inter alia, on the available electronic component speed, the processing speed of the processor/controller 44 and the specific application type. For example, the pulse duration and pulse interval of FIGS. 8a and 8b can have the values of 0.6 milliseconds and 15.6 milliseconds, respectively, and the two periods 76 and 78 of FIG. 9 may each have the value of 300 microseconds.

It is further noted that, while in the embodiment disclosed hereinabove (FIGS. 8a, 8b and 9) a DC gain correction procedure is performed for each first time period 76 as disclosed in detail hereinabove, it was found that the DC correction can be performed much less often with no deterioration of the devices performance and in some cases with a resulting improvement of measurement stability. For example, if a typical measurement cycle lasts approximately 4-5 seconds, in order to include a few heart pulse cycles, and includes 256 infrared and red light measurement periods (each of the light measurement periods comprising the time periods 76 and 78), performing the DC correction procedure only once for every 256 measurement periods (i.e. once for each measurement cycle) results with a better stability. Thus, the number of times of performing the DC correction procedure of the present invention per measurement cycle may be varied for optimizing the stability and accuracy of the measurements. The optimal number of times of performing the DC correction procedure of the present invention per measurement cycle may depend, inter alia, on the optical parameters of the light source 16 and the detector 18 of the device 10 and on the specific wavelengths implemented in the specific application.

An advantage of reducing the number of DC corrections per measurement cycle is that it reduces the computational load of the CPU 44, enabling increasing the number of light measurement time periods within each given measurement cycle or, alternatively, using a less powerful CPU 44 to reduce the overall cost of the device 10 while conserving or even improving the accuracy and stability of the measurements.

The gain amplification factors are selected from a set of preselected values. Amplifier A1, which acts to amplify the DC signal component, can have gain amplification factors of 1, 2, 4 or 8. Amplifier A2, which amplifies the AC signal component, operates in the amplification ranges of 1, 10, 100 or 1000.

An advantage of the ability to automatically switch between the gain amplification factors based on the iterative process performed by CPU 44, is that it allows the device 10 to obtain oximetry measurements in different parts of the body without recalibrating the gain amplification factor for each area.

The separated AC and DC signals are calibrated using the formulas:

$$V_{AC} = (V_{a/d}) K / (A_{AC} * A_{DC})$$

$$V_{DC} = (V_{a/d}) K / (A_{AC} * A_{DC})$$

where $V_{a/d}$ is the signal from the analog to digital converter and $A_{AC}$ and $A_{DC}$ represent the gain of the A2 and A1 amplifiers, respectively. Using these calibration equations it is possible to calculate a value for each of the signal components ($V_{AC}$ and $V_{DC}$), which is substantially separated from the other signal component.

Once the AC and DC signal components are calibrated, calculations for purposes of determining oxygen saturation are performed by taking the AC and DC values for each wavelength and forming a ratio:

$$G = \frac{V(AC)_{red} / V(DC)_{red}}{V(AC)_{infrared} / V(DC)_{infrared}}$$

This ratio is used to calculate the oxygen saturation in the formula:

$$SatO_2 = B - A*G$$

where B and A are constants. CPU 44 determines whether or not this value falls within the desired window, and in cases where the value is unacceptable and stress is detected, an output signal 47 is sent to alarm 48 and the alarm will turn on. Alternatively, or in addition, the output signal 47 can be sent to RF transmitter 50 for transmission to receiver 60. Additional information, such as a log of all readings, may be sent from CPU 44 as a data output signal 53 to PC 52.

In summary, the physiological stress detector device of the present invention provides a non-invasive method for more accurately measuring blood constituents in a compact, easily utilized design. It is especially useful for application in SIDS monitoring systems due to its compact lightweight design, which is provided with no cumbersome, dangerous cable connections.

An advantage of the devices and methods of the present invention is that the sensitivity and improved signal to noise ratio of the present method enables use of transmitted methods of pulse oximetry under conditions where the signals are of low amplitude relative to the noises. In a non-limiting example, the method and devices may be particularly useful for transmitted oximetry under conditions of low blood perfusion such as in systemically shocked patients or in cases of severe hypothermia.

A major advantage of the present invention is in its application to reflective oximetry where the signals are usually of relatively low amplitude. In particular, the sensitivity of the method and the devices may enable performing reflective pulse oximetry on regions of the body, which exhibit particularly low amplitude signals such as the wrist region, or the ankle region of adults and babies.

Figure 10:
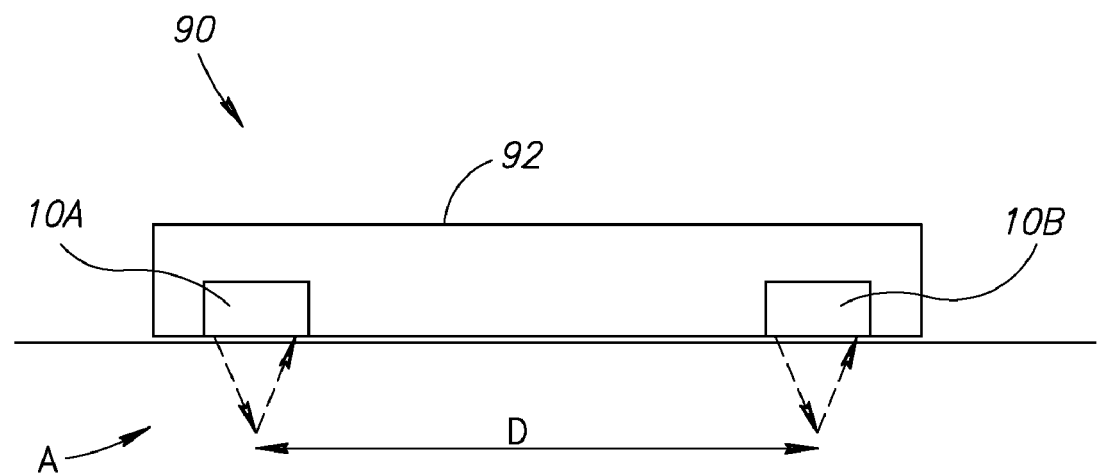
FIG. 10 is a schematic illustration of a device for determining blood flow velocity in accordance with another preferred embodiment of the present invention.

Reference is now made to FIG. 10, which is a schematic illustration of a device 90 for determining blood flow velocity in accordance with another preferred embodiment of the present invention.

The device 90 includes a housing 92 and two pulse oximetry devices 10a and 10b attached thereto. The devices 10a and 10b are constructed as the device 10 disclosed hereinabove and are simultaneously operated to provide an amplified pulse oximetry AC signal as disclosed in detail for the device 10 hereinabove. The fixed distance D between the device 10a and the device 10b is represented by the double-headed arrow labeled D. The device 90 is placed on a region of skin A and the pulse oximetry AC signal is simultaneously determined for each of the devices 10a and 10b.

Figure 11:
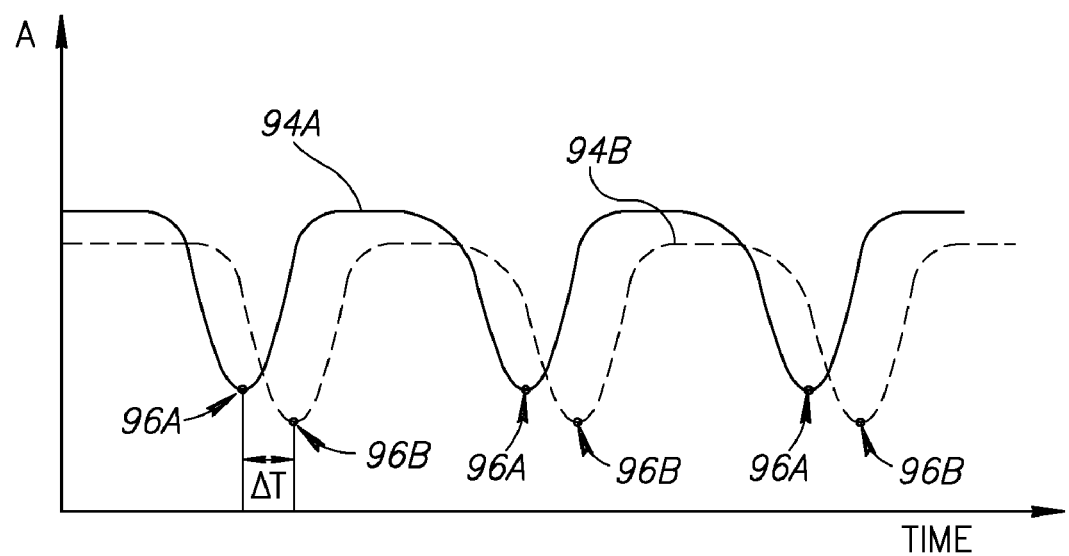
FIG. 11 is a schematic graph useful in understanding the method of determining blood flow velocity used by the device of FIG. 10.

Reference is now made to FIG. 11, which is a schematic graph useful in understanding the method of determining blood flow velocity used by the device 90 of FIG. 10. The horizontal axis represents time and the vertical axis represents the amplitude of the reflective oximetry AC signals. The curve 94A represents the AC signal output from the device 10a and the curve 94B represents the AC signal output from the device 10b. The minima 96A and 96B of the curves 94A and 94B, respectively represent the minima of the reflected AC signal due to the pulsation of the blood flow. The time delay ΔT between the reflection minima 96A and 96B represent the time delay between the registration of a minimum reflectance by the device 10a and its registration by the device 10b. The delay results from the finite blood velocity and the distance D separating the devices. Since the distance D between the devices 10a and 10b is known, the approximate blood flow velocity V can be determined by calculating the value $$V=D/\Delta T.$$

The processing unit 40 of one of the devices 10a or 10b thus acquires two data sets. The first data set represents the AC signal component of the device 10a and the second data set represents the AC signal component of the device 10b. Preferably, both of the data sets are digital data sets and are sampled simultaneously. The data sets are sampled such that each data set includes at least one extremum data value corresponding to a minimum or a maximum value of the AC signal component, the processing unit 40 detects the extremum point for each of the data sets using any method known in the art for detecting an extremum point. The processing unit then calculates the time interval ΔT between the corresponding extremum points of the first and the second data sets and calculates the blood flow velocity from the ratio ΔT/D.

Preferably, for devices using reflective pulse oximetry of the present invention, the extremum data values used are minimum values representing minimal values of reflected light due to maximal absorption of the light from the light sources 16 of the devices 10a and 10b. However, the extremum values may also be maxima. For example, in an embodiment where transmitted pulse oximetry devices are used, the extremum values may be maxima.

It is noted that, while each of the devices 10a and 10b may have a CPU 44 as disclosed hereinabove, in accordance with another preferred embodiment of the present invention, the device 90 may include a single CPU unit (not shown) which may be shared for performing all the calculations and control functions disclosed hereinabove for the operation of each of the devices 10a and 10b and for additionally performing the determination of ΔT and the calculation of the approximate blood flow velocity therefrom.

It will be appreciated by those skilled in the art that suitable methods for detecting and timing the reflection minima 96A and 96B are well known in the art and are not included in the subject matter of the present invention, and will therefore not be described herein in detail.

It is noted that while the device and method for determining blood flow velocity disclosed hereinabove is adapted for use with a pair of devices 10a and 10b, a larger number of devices (not shown) may be used together either as a multiplicity of device pairs or in any other geometrical configuration for improving the accuracy of the measurement by averaging the results of multiple pair determinations or by any other suitable computational method known in the art.

It is noted that, while the preferred embodiments of the present invention are particularly adapted for reflective pulse oximetry applications, it may be also implemented in many other applications. For example, the method and the device of the present invention may be adapted to the monitor billirubin levels for the detection and monitoring of jaundice, by suitably selecting a light source which emits wavelengths of light in the range selectively absorbed by billirubin, (approximately between 400-600 nanometer).

In another example, the present invention may also be used to detect and monitor blood constituents, which have distinct absorbance peaks in the visible, range, the near ultraviolet (UV) range or in both the visible and the near UV range. For this type of applications one or more of the light wavelengths used may be obtained from a gas discharge lamp or from any another suitable source of light in the near UV range.

Another application of the present invention is the application of the method for the determination and mapping of areas of organs suspected of a reduced blood flow due to chronic or temporary clinical condition. For example if an internal or external organ is suspected to have developed gangrene the device 10 of the present invention may be used to map areas having low or reduced blood flow by moving the device 10 along the organ and in contact therewith and mapping areas of reduced blood flow by recording and mapping the amplitude of the minima of the pulse oximetry AC component as disclosed hereinabove along the surface of the organ. This method may be particularly useful in mapping of such reduced flow areas in cases where regular transmitted pulse oximetry is not applicable due to inaccessibility problems or due to very noisy signal conditions.

One exemplary application is mapping the external surface of the intestines using a small pre-sterilized reflective oximetry device such as the device 10 of the present invention. In such a case transmitted oximetry devices cannot be used because it is not possible to position a light source and a light detector on opposite sides of the intestinal wall. The device 10 is particularly advantageous here because it can be simply moved along the external surface of the suspected intestinal part and because of its improved sensitivity and reduced noise level.

The above mapping method may be applied to many other organs such as limbs suspected of blood flow disturbances due to a gangrene condition or other diseases.

It is noted that the devices of the present invention may be implemented in a variety of different configurations. The devices 10 or 90 of FIGS. 1 and 10, respectively may be connected to a computer (not shown) or a monitor (not shown). The computer or monitor may include a display device (not shown).

An alternative configuration may include the device 10, connected to a housing(not shown) wirelessly or by suitable wires. The housing may also include a liquid crystal display device (LCD), such as the LCD display model G1216001N000-3D0E, commercially available from Seiko Instruments Inc., Japan, suitably connected to the CPU 44 for displaying alphanumeric symbols representative of one ore more parameters of the pulse oximetry signal such as the pulse frequency , or amplitude or any other data. The LCD display may also display the AC signal graphically with or without the alphanumeric data.

In a third configuration of the device of the present invention the pulse oximetry device includes all the optical and electronic components within one single device shaped as a wristwatch like device to be worn as a self-contained unit. One non-limiting example (not shown) is a device worn on the wrist and shaped like a wristwatch. All the components of the device 10 are integrated within the device such that the light source 16 and the detector 18 are attached to the device so as to be in contact with the skin when the device is worn. All the necessary electronic components disclosed hereinabove are also integrated in the device including a power source such as a battery. The device may thus monitor signals, may or may not collect and store data and may or may not activate an alarm unit or transmit a distress signal as disclosed hereinabove in detail. It is noted that this self contained integrated device configuration may also be shaped to be placed in contact with the skin on the limbs, forehead or any other organ of the patient by suitable means such as strips bands of flexible material, adhesives or any other suitable attachment means known in the art.

The self-contained integrated device configurations may be used for a variety of applications. For example, in a preferred embodiment of the present invention, the device may determine the pulse rate of the wearer. It is known that during a meal the pulse rate increases. The pulse rate may thus be used for diet control by reporting to the user when the pulse rate reaches a predetermined value or when the increase in the pulse rate following the beginning of a meal is within a predetermined rate. The user may thus use the device for obtaining an indication of when to stop consuming food.

The device may also be used for radial pulse measurement in cardiac measurements and for various bio-feedback applications.

Figure 12A:
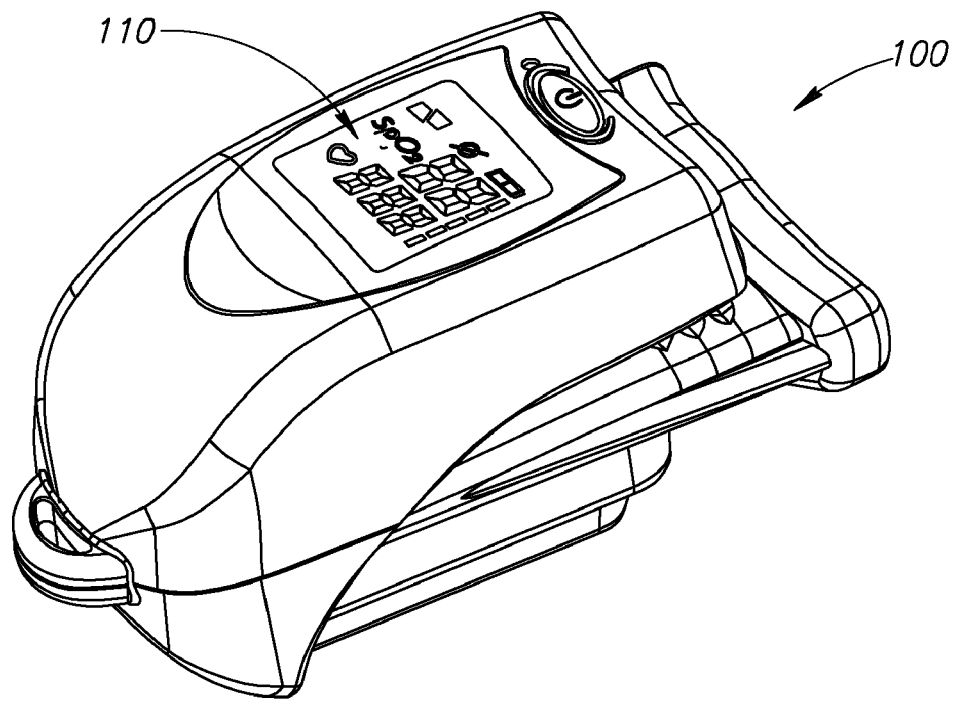
FIGS. 12*a*-12*c* are schematic illustrations of an exemplary application of a device for determining blood saturation and heart pulse rate according to an embodiment of the invention.
Figure 12B:
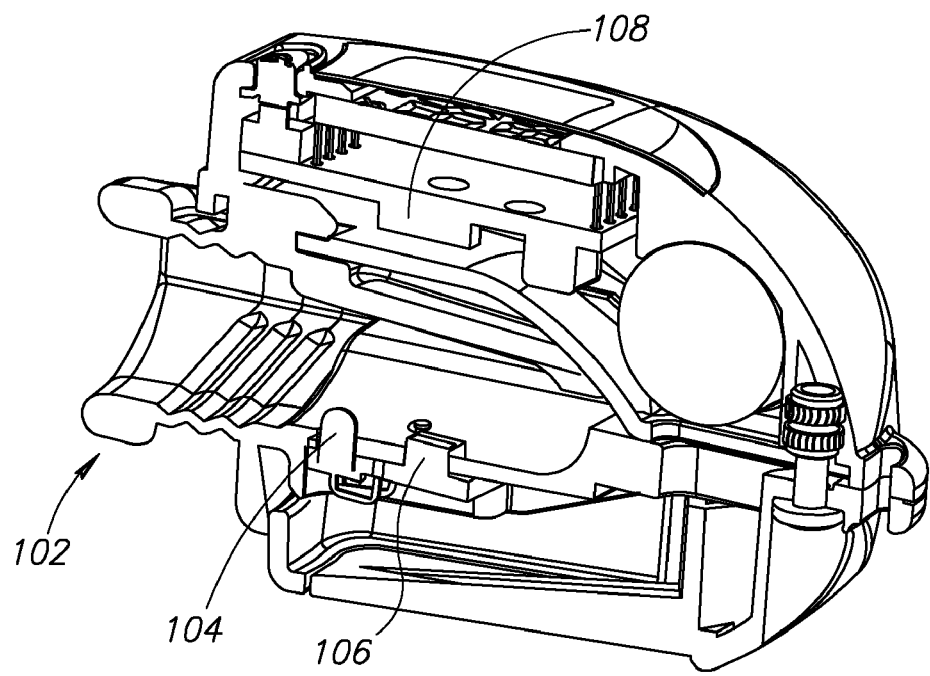
Figure 12C:
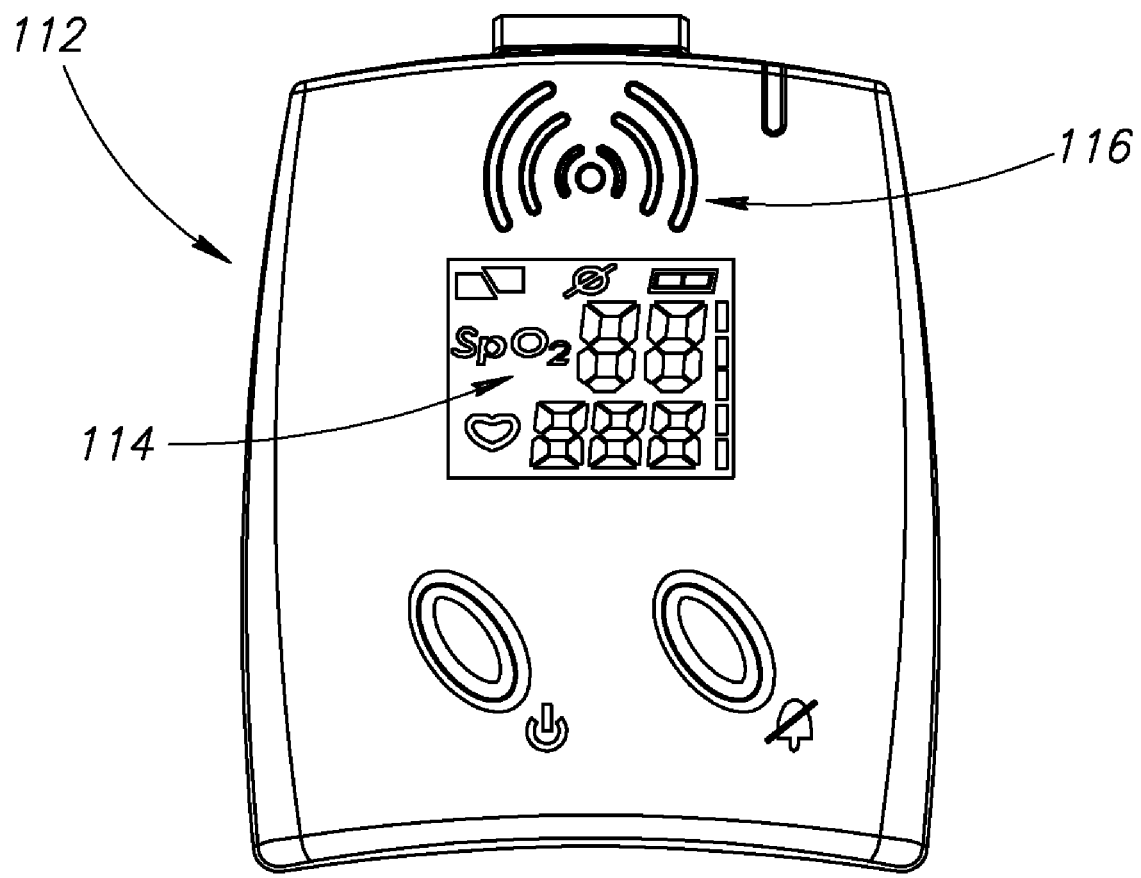

Reference is now made to FIGS. 12a-12c, which illustrate an exemplary application of an oximetry device according to an embodiment of the invention. Finger oximetry device, generally designated 100, may be configured for measuring blood saturation and heart pulse rate. FIG. 12a is an isometric top view of the device 100 and FIG. 12b is a sectional cutaway illustration of the device.

Device 100 comprises a housing 102 configured to receive a digit such as a finger. The housing 102 comprises a light source 104 (similar to light source 16 of FIG. 1 ) a detector 106 (similar to detector 18) and a processing unit 108.

The processing unit 108 is integrated with the detector 106 so that processing of signals is carried out within the device 100. Device 100 may also comprise a display unit 110 for displaying the output of the blood saturation and heart pulse rate measurements. The output may comprise data and/or a graphic display such as a waveform, for example.

In an alternative embodiment, a disposable insert may be may be used within the finger housing. In another alternative embodiment, the device 100 may be linked by a cable to an external processing unit.

The device 100 may further comprise a transmitter (not shown) for transmitting the output signals to a remote monitoring station 112, (an example of which is shown in FIG. 12c). The remote monitoring station 112 may also include display unit 114. The remote monitoring station 112 may be configured to activate an audio or visual alarm 116, for example, when the blood saturation or heart pulse rate falls outside of a pre-determined range.

In an alternative embodiment, the device 100 may be utilized together with a personal digital assistant (PDA), for example, which may be configured to receive the transmitted signals. The PDA would effectively act as the remote monitoring station.

Figure 13A:
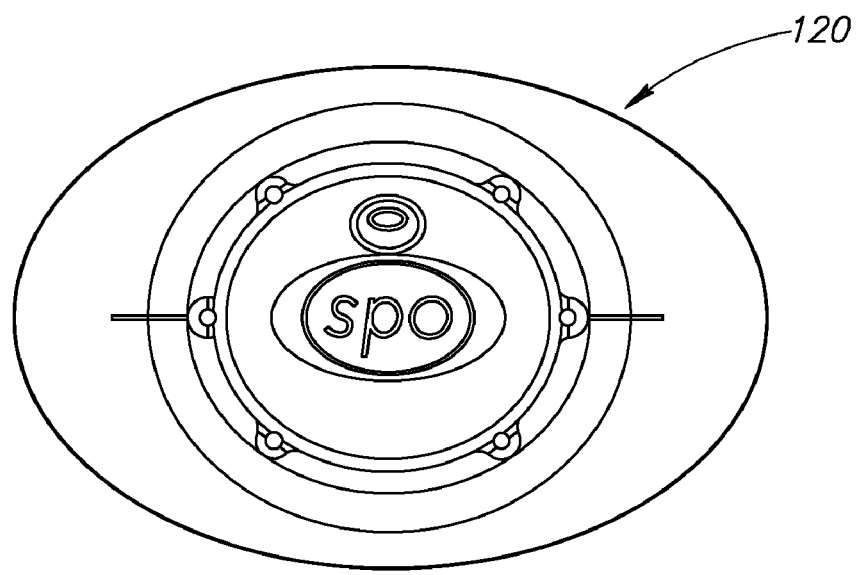
FIGS. 13*a*-13*b* are schematic illustrations of an exemplary application of a device for determining blood saturation and heart pulse rate according to another embodiment of the invention.
Figure 13B:
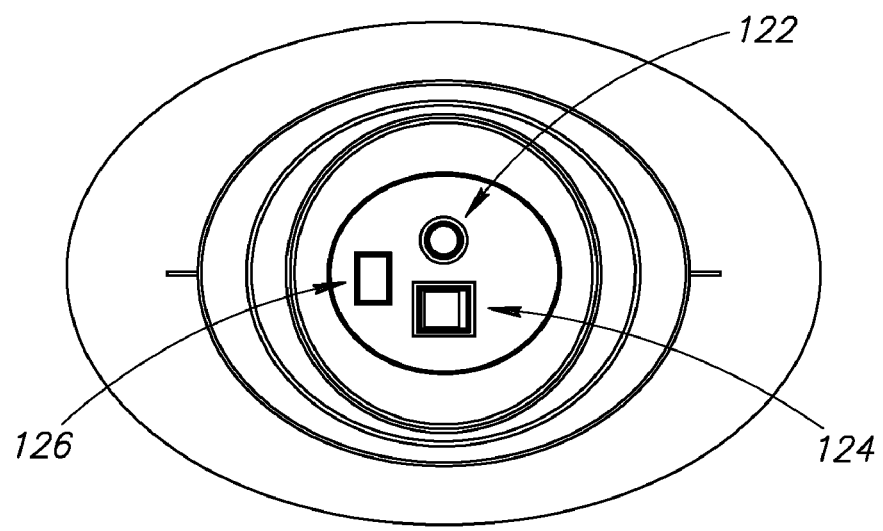

Reference is now made to FIGS. 13a and 13b, which illustrate the front and rear faces, respectively of an embodiment of the invention in the form of a stand-alone wireless device 120. Device 120 comprises a light source 122 and a detector 124. Light source 122 and detector 124 are similar to light source 16 and detector 18 of FIG. 1. A processor 126 may be added.

Device 120 may also comprise a transmitter (not shown) for transmitting data to a monitor such as PDA, for example, or any other receiving device thus allowing data to be transferred conveniently and speedily to the physician's or the caregiver's PDA. The PDA thus converts a plain pulse-oximeter, for example, without display and accessories to a complete measuring system. The PDA may also display the date in waveform.

The device 120 may also have adhesive tape attached to its rear face so that the device may be attached to a convenient part the skin.

In an alternative embodiment, the device ,the device 120 may be wired directly to a PDA or any other receiving device.

Reference is now made to FIGS. 14a-14c, which illustrate an exemplary application of the device according to an embodiment of the invention, generally designated 140, configured in the form of a pen. Device 140 comprises a light source 142 and a detector 144. Light source 142 and detector 144 are similar to light source 16 and detector 18 of FIG. 1. In addition, the pen device 140 may further comprise a display unit 146 for displaying the output of the blood saturation and heart pulse rate measurements, for example.

The sensor comprising the detector 144 and light source 142 may be located at the edge of the pen or at its side, for example. To obtain a reading, the detector 144 is placed on the subject's skin such as the forehead. The readings may be displayed on the display unit thereby allowing the physician, nurse or any caregiver to speedily obtain an indication of the subject's blood saturation and heart pulse rate in a manner similar to obtaining a patient's temperature.

Figure 15A:
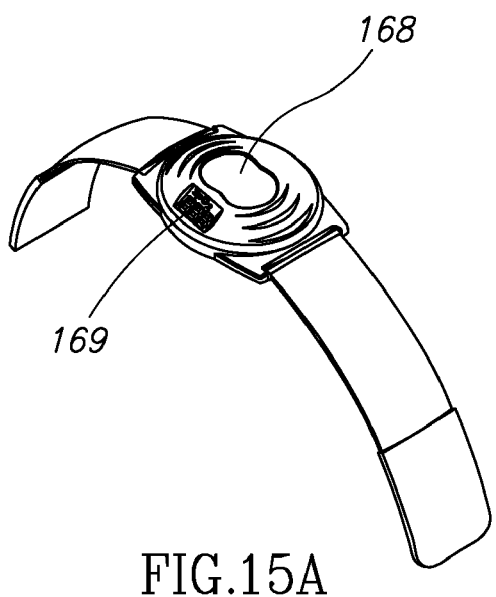
FIGS. 15*a*-15*c* are schematic illustrations of an exemplary application of a device for determining blood saturation and heart pulse rate according to another embodiment of the invention.
Figure 15B:
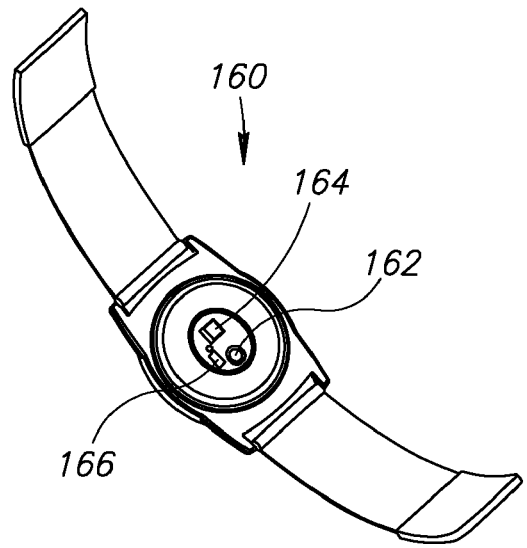

Reference is now made to FIGS. 15a and 15b, which illustrate an exemplary application of the device according to an embodiment of the invention, generally designated 160, configured as a wristwatch. Wristwatch device 160 comprises a light source 162 and a detector 164 located on the rear face of the watch. Light source 162 and detector 164 are similar to light source 16 and detector 18 of FIG. 1. The wristwatch 160 may further comprise a processing unit 166 and an alerter 168.

The wearer may summon help by pressing on the alerter 168, which transmits an alert to a receiving station, such as a PDA, for example. The watch device may also transmit data regarding the wearer's blood saturation and heart pulse rate for example, thus informing the caregiver of the wearer's health state. Knowing the health state of the sender enables the physician or caregiver to determine the urgency of the situation and determine the appropriate action to take.

It will be appreciated by persons knowledgeable in the art that other vital signals, such as temperature, billirubin may be measured and displayed.

The processing unit 166 is integrated with the detector 164 so that processing of signals is carried out within the device 160. A display unit 169 may also be placed on the front face for displaying the output of the blood saturation and heart pulse rate measurements.

In an alternative embodiment of the invention, the wrist watch 160 may also further comprise an alert device (not shown) activated in the event that either the blood saturation or heart pulse rate, for example, falls outside of a pre-determined range, to transmit data to a receiving station such as a PDA.

Figure 15C:
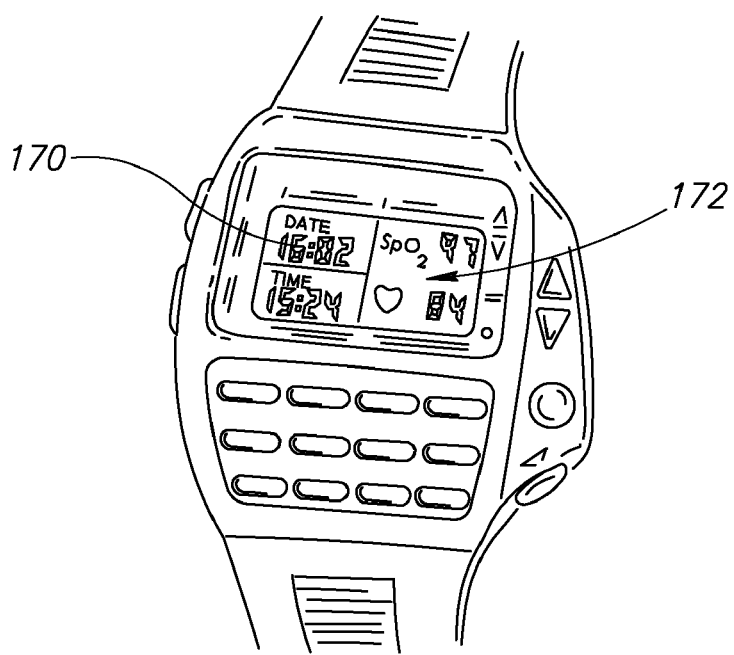

In a further embodiment of the wristwatch device, shown in FIG. 15c, the front face of the watch may be configured to include standard watch display 170 such as time and date as well as indications of the blood saturation or heart pulse rate 172. This type of watch is useful for sportsmen, military personnel firemen and other active persons, for example.

In a further embodiment of the wristwatch device, the faces of the watch may be reversed so that the sensor device (light source 162, and detector 164) is placed on the front face. The back face may be left plain or contain the transmitter 166. The front face may be configured to measure blood constituents from the wearer's finger, for example.

Figure 16A:
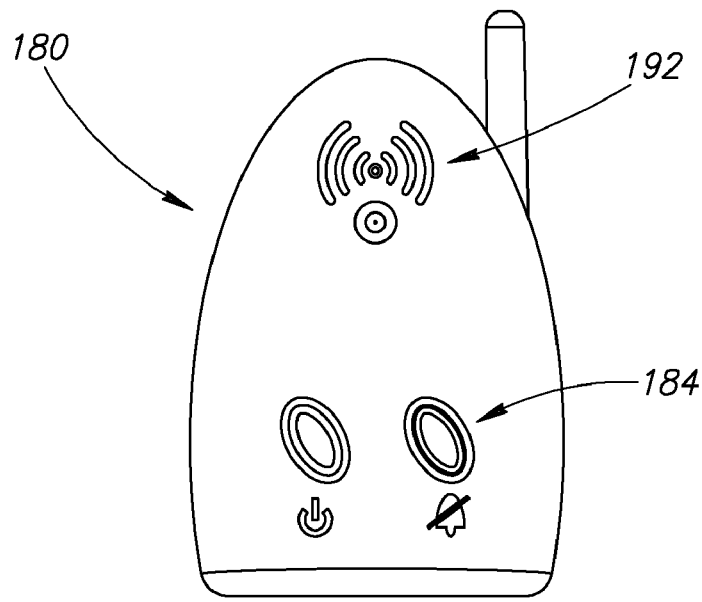
FIGS. 16*a*-16*c* are schematic illustrations of a monitoring system according to an embodiment of the invention.
Figures 16B, 16C:
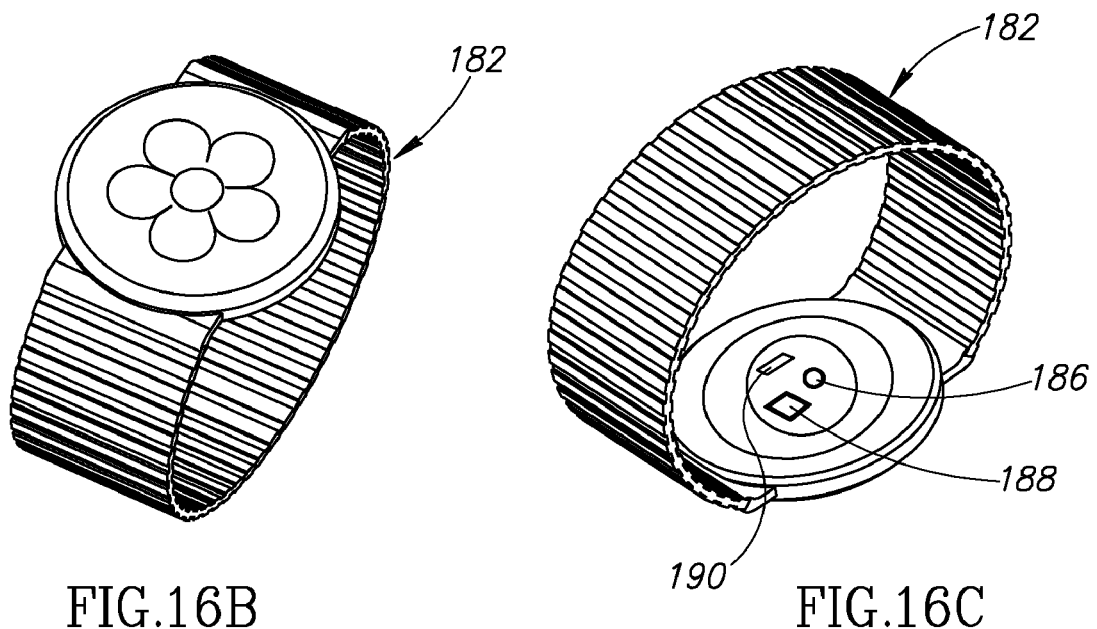

Reference is now made to FIGS. 16a-16c, which illustrate a monitoring system, generally designated 180. The monitoring system comprises a bracelet 182 configured to fit a foot or arm and a base station 184.

The bracelet 182 comprises a light source 186 and a detector 188 located on the rear face of the bracelet. Light source 186 and detector 188 are similar to light source 16 and detector 18 of FIG. 1. The bracelet 182 may further comprise a processing unit 190 and a transmitter (not shown). The processing unit 190 may be integrated with the detector 188.

The base station 184 is located at a remote location from the bracelet 182 to receive the output signals from the bracelet in real time indicating the blood saturation or heart pulse rate. The base station 184 may be configured to activate an audio or visual alarm (for example) when the blood saturation or heart pulse rate falls outside of a pre-determined range. Furthermore, the base station 184 may display the signals received as data and./or in a waveform in addition as an alarm, The monitoring system is wireless and is suitable for use with a young baby, for example, since there is not any danger to the baby from cables being wrapped around the baby.

Figure 17A:
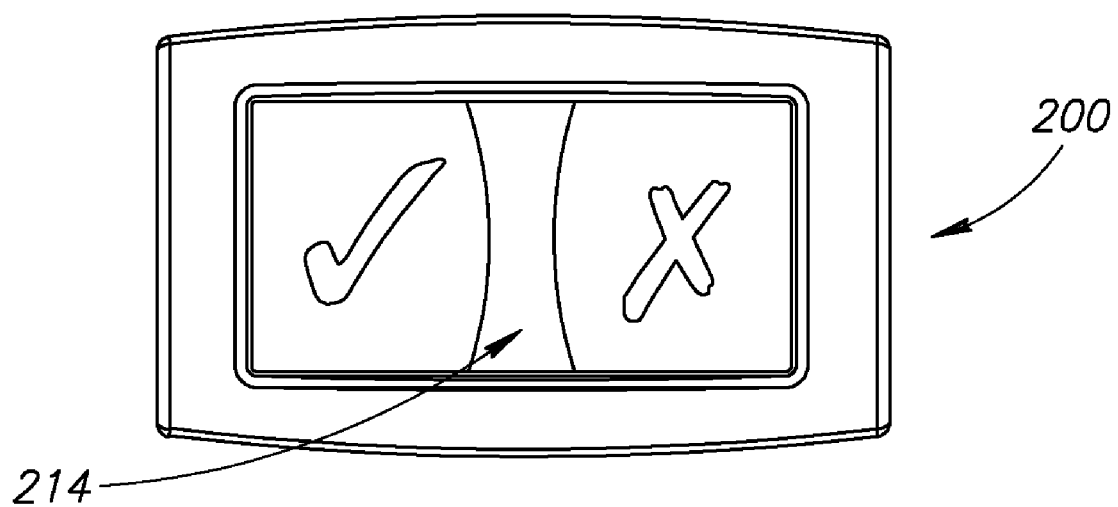
FIGS. 17*a*-17*b* are schematic illustrations of a monitoring system according to another embodiment of the invention.
Figure 17B:
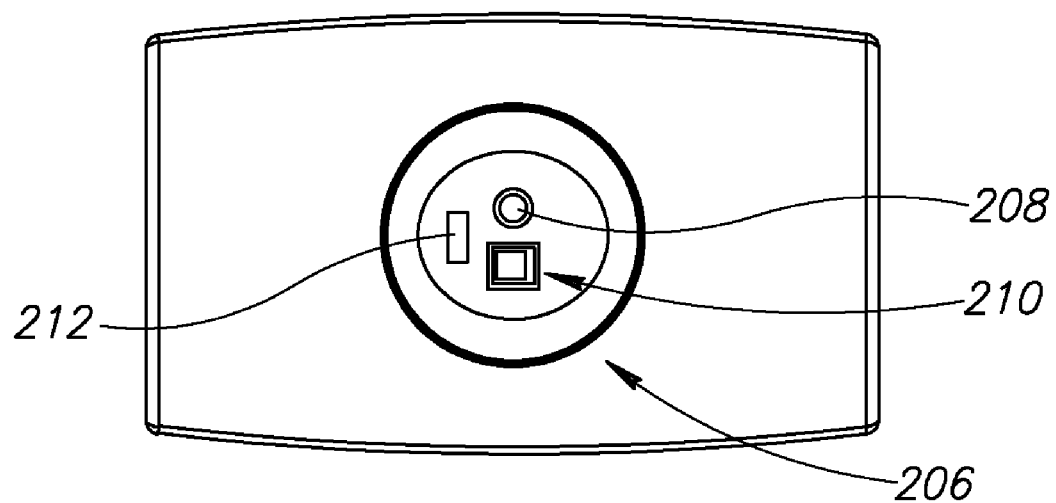

In an alternative application, a monitoring device 200, illustrated in FIGS. 17a-17b is illustrated. The monitoring device 200 may be combined with protective masks, such as search and rescue masks, gas masks, and anti biological and chemical masks. The monitoring device 200 comprises a tag having a display unit on its front face 204 and a measuring device 206 comprising a light source 208 and a detector 210 located on the rear face of device 200. Light source 208 and detector 210 are similar to light source 16 and detector 18 of FIG. 1. The device 200 may further comprise a processing unit 212 for processing the output from the detector 210.

The rear face of the device 200 may be adhesive and may be placed proximate to the skin of the wearer to measure blood saturation and heart pulse rate. The front face of the device 200 comprises a display unit 214, which may comprise green and red LEDs, to indicate well-being and that help is needed, respectively. Alternatively, indicators, such as the "√" and "X" could be used together with the green and red LEDs.

In an alternative embodiment, for example for persons wearing a protective suitor mask, the display unit may be a separate unit in communication with the sensor device containing the light source 208 and a detector 210, In this case, the sensor device would be placed on the body of the wearer.

Figure 18A:
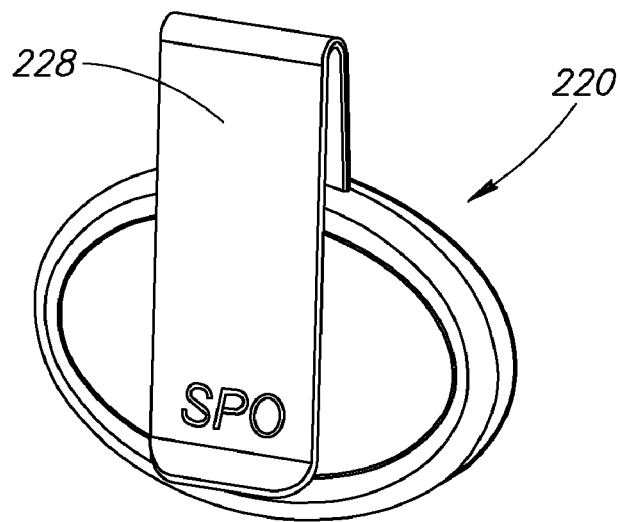
FIGS. 18*a*-18*c* are schematic illustrations of an exemplary application of a device for determining blood saturation and heart pulse rate according to another embodiment of the invention.
Figures 18B, 18C:
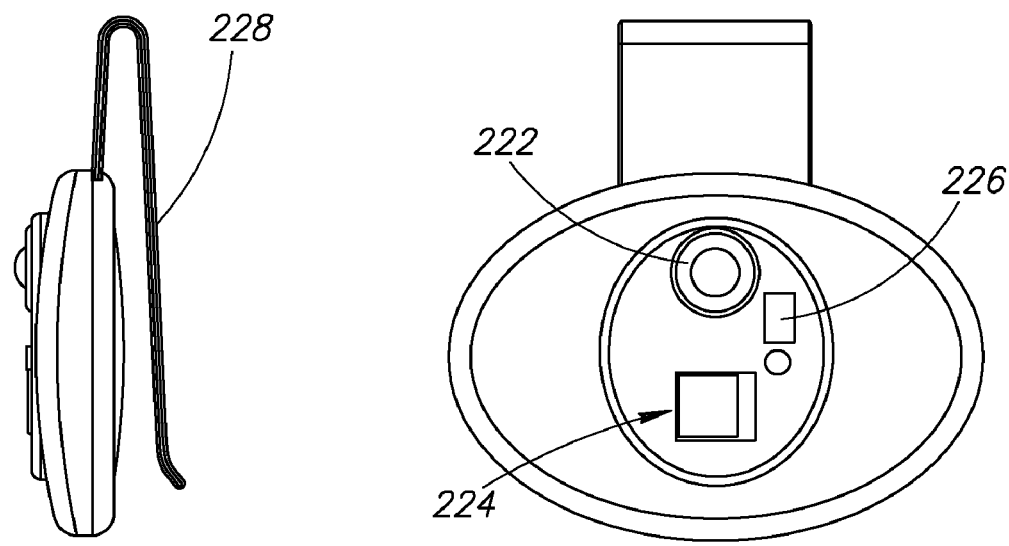

Reference is now made to FIGS. 18a-18c, which a further embodiment of the invention in the form of a tag device 220. Tag device 220 comprises a light source 222 and a detector 224 on its rear face. Light source 222 and detector 224 are similar to light source 16 and detector 18 of FIG. 1.

Tag device 220 may also comprise a transmitter 226 for transmitting data to a PDA, for example, or any other receiving device thus allowing data to be transferred conveniently and speedily to the physician's or caregiver's PDA. The PDA thus converts a plain pulse-oximeter, for example, without display and accessories to a complete measuring system.

The tag device 220 may also have a "U" type spring clip 228 suitably attached to the device. The clip 228 extends over the front face of the device. In use, the clip is suitably attached to a wearer's clothing, for example, so that the rear face of the device is placed proximate to a convenient part the skin for measuring of blood constituents.

In alternative embodiments, the tag device 220 may be fitted to the inside of a bandana, cap or hat so that the device is proximate the wearer's skin while also being hidden from view. It may also be fitted to a baby's diaper, for example. The tag device may also be configured to measure/display other constituents such as temperature.

It will be appreciated by persons knowledgeable in the art, that though the various applications described hereinabove with reference to FIGS. 12-18 refer to the measurement of blood saturation and heart pulse rate, the applications are also applicable for the measurement of any blood constituent.

In all of the above applications of the self contained integrated device configurations, such as a bracelet-like device or the like the device has an advantage of being a compact, lightweight and convenient wearable device while still providing the high sensitivity, accuracy and relative immunity to movement artifacts of the present invention.

It is noted that the devices of the present invention, as used in the various applications disclosed herein above, may also be configured and used as monitoring devices in a hospital environment, as well as for domestic use. It is further noted that the devices and methods of the present invention may be adapted for use of humans and animals.

Having described the invention with regard to certain specific embodiments thereof, it is to be understood that the description is not meant as a limitation, since further modifications will now become apparent to those skilled in the art, and it is intended to cover such modifications as fall within the scope of the appended claims.

What is claimed is:

1. A non-invasive device for measurement of blood saturation and heart pulse rate, comprising:
   a housing unit configured to be attachable to a head covering disposed proximate to an organ being measured, said head covering comprising one of a group including a cap, a hat and a bandanna, said housing unit comprising:
      at least one light source, providing light directed toward the surface of said organ, the light being reflected from said organ;
      a light detector spaced apart from said at least one light source and being sensitive to intensity levels of said reflected light for producing intensity signals in accordance therewith; and
   a processing unit for processing said intensity signals received from said light detector for producing output signals, said processing unit comprising:
      first and second amplifiers for amplifying said intensity signals, each in accordance with a respective first and second gain amplification factor; and
      a processor for automatically determining said first and second gain amplification factors in adjustable fashion;
      wherein during a first stage, said first and second amplifiers amplify a DC signal component of said intensity signals in accordance with predetermined first and second gain amplification factors, said amplified DC signal component being subtracted from said intensity signals at an input of said first amplifier, to isolate an AC signal component of said intensity signals,
      and wherein during a second stage, said second amplifier amplifies said isolated AC signal component in accordance with said adjustably-determined second gain amplification factor,
   said processing unit producing output signals in accordance with said isolated AC signal component and said DC signal component and calculating in accordance therewith, at least one blood constituent level.

2. The device according to claim 1, wherein said processing unit comprises mapping means for mapping the intensity of said AC signal component along the surface of said organ to detect regions of said organ having a reduced blood flow.

3. A non-invasive device for measurement of blood saturation and heart pulse rate, comprising:

a housing unit configured to be attachable to a head covering, said head covering disposed proximate to an organ being measured, said head covering comprising one of a group including a cap, a hat and a bandanna, said housing unit comprising:
  at least one light source, providing light directed toward the surface of said organ, the light being reflected from said organ;
  a light detector spaced apart from said at least one light source and being sensitive to intensity levels of said reflected light for producing intensity signals in accordance therewith; and
a processing unit for processing said intensity signals received from said light detector for producing output signals,
wherein processing the intensity signals is done through a signal analog path, said processing unit comprising:
  first and second amplifiers for amplifying said intensity signals, each in accordance with a respective first and second gain amplification factor; and
  a processor for automatically determining said first and second gain amplification factors in adjustable fashion;
  wherein during a first stage, said first and second amplifiers amplify a DC signal component of said intensity signals in accordance with predetermined first and second gain amplification factors, said amplified DC signal component being subtracted from said intensity signals at an input of said first amplifier, to isolate an AC signal component of said intensity signals,
  and wherein during a second stage, said second amplifier amplifies said isolated AC signal component in accordance with said adjustably-determined second gain amplification factor,
said processing unit producing output signals in accordance with said isolated AC signal component and said DC signal component and calculating in accordance therewith, at least one blood constituent level.

4. A system comprising:
a non-invasive device for measurement of blood saturation and heart pulse rate, comprising:
a housing unit configured to be attachable to a head covering, said head covering disposed proximate to an organ being measured, said head covering comprising one of a group including a cap, a hat and a bandanna, said housing unit comprising:
  at least one light source, providing light directed toward the surface of said organ, the light being reflected from said organ;
  a light detector spaced apart from said at least one light source and being sensitive to intensity levels of said reflected light for producing intensity signals in accordance therewith;
  a processing unit for processing said intensity signals received from said light detector for producing output signals; and
  a transmitter configured to transmit said output signals to a receiver at a remote location; and
  a receiver configured to indicate an alert when the blood saturation or heart pulse rate falls outside of a pre-determined range;
wherein said processing unit comprises:
  first and second amplifiers for amplifying said intensity signals, each in accordance with a respective first and second gain amplification factor; and
  a processor for automatically determining said first and second gain amplification factors in adjustable fashion;
  wherein during a first stage, said first and second amplifiers amplify a DC signal component of said intensity signals in accordance with predetermined first and second gain amplification factors, and wherein the amplified DC signal component is converted by a digital to analog converter to an analog signal and is subtracted from the intensity signals, said amplified DC signal component being subtracted from said intensity signals at an input of said first amplifier, to isolate an AC signal component of said intensity signals,
  and wherein during a second stage, said second amplifier amplifies said isolated AC signal component in accordance with said adjustably-determined second gain amplification factor,
said processing unit producing output signals in accordance with said isolated AC signal component and said DC signal component and calculating in accordance therewith, at least one blood constituent level.

5. A system comprising:
a non-invasive device for measurement of blood saturation and heart pulse rate, comprising:
a housing unit configured to be attachable to a head covering, said head covering disposed proximate to an organ being measured, said head covering comprising one of a group including a cap, a hat and a bandanna, said housing unit comprising:
  at least one light source, providing light directed toward the surface of said organ, the light being reflected from said organ;
  a light detector spaced apart from said at least one light source and being sensitive to intensity levels of said reflected light for producing intensity signals in accordance therewith;
  a processing unit for processing said intensity signals received from said light detector through a signal analog path thereby producing output signals; and
  a transmitter configured to transmit said output signals to a receiver at a remote location; and
a receiver configured to indicate an alert when the blood saturation or heart pulse rate falls outside of a pre-determined range,
said processing unit comprising:
  first and second amplifiers for amplifying said intensity signals, each in accordance with a respective first and second gain amplification factor; and
  a processor for automatically determining said first and second gain amplification factors in adjustable fashion;
  wherein during a first stage, said first and second amplifiers amplify a DC signal component of said intensity signals in accordance with predetermined first and second gain amplification factors, said amplified DC signal component being subtracted from said intensity signals at an input of said first amplifier, to isolate an AC signal component of said intensity signals,
  and wherein during a second stage, said second amplifier amplifies said isolated AC signal component in accordance with said adjustably-determined second gain amplification factor,
  said processing unit producing output signals in accordance with said isolated AC signal component and said DC signal component and calculating in accordance therewith, at least one blood constituent level.

6. A system comprising:
a non-invasive device for measurement of blood saturation and heart pulse rate, comprising:
a housing unit configured to be attachable to a head covering, said head covering disposed proximate to an organ being measured, said head covering comprising one of a group including a cap, a hat and a bandanna, said housing unit comprising:
at least one light source, providing light directed toward the surface of said organ, the light being reflected from said organ;
a light detector_spaced apart from said at least one light source and being sensitive to intensity levels of said reflected light for producing intensity signals in accordance therewith, said light detector being unaffected by shunted or coupled light from said light source;
a processing unit for processing said intensity signals received from said light detector through a signal analog path thereby producing output signals; and
a transmitter configured to transmit said output signals to a receiver at a remote location; and
a receiver configured to indicate an alert when the blood saturation or heart pulse rate falls outside of a pre-determined range;
wherein said processing unit comprises:
first and second amplifiers for amplifying said intensity signals, each in accordance with a respective first and second gain amplification factor; and
a processor for automatically determining said first and second gain amplification factors in adjustable fashion;
wherein during a first stage, said first and second amplifiers amplify a DC signal component of said intensity signals in accordance with predetermined first and second gain amplification factors, and wherein the amplified DC signal component is converted by a digital to analog converter to an analog signal and is subtracted from the intensity signals, said amplified DC signal component being subtracted from said intensity signals at an input of said first amplifier, to isolate an AC signal component of said intensity signals,
and wherein during a second stage, said second amplifier amplifies said isolated AC signal component in accordance with said adjustably-determined second gain amplification factor,
said processing unit producing output signals in accordance with said isolated AC signal component and said DC signal component and calculating in accordance therewith, at least one blood constituent level.

7. The system according to claim 6 wherein said processor develops a control signal when said adjustably-determined second gain amplification factor is established in said second stage, said control signal is able to shut off said light source.

8. The system according to claim 7 wherein said control signal conserves energy by reducing the operational duty cycle of said at least one light source.

9. The system according to claim 6 wherein said first and second gain amplification factors are determined by said processor in an iterative process by adjustably setting a gain amplification factor and measuring a dynamic voltage range of said output signals to determine if said voltage range falls within a predetermined window established by said processor.

10. A non-invasive device for measurement of blood saturation and heart pulse rate, comprising:
a housing unit configured to be attachable to a head covering, said head covering disposed proximate to an organ being measured, said head covering comprising one of a group including a cap, a hat and a bandanna, said housing unit comprising:
at least one light source, providing light directed toward the surface of said organ, the light being reflected from said organ;
a light detector spaced apart from said at least one light source and being sensitive to intensity levels of said reflected light for producing intensity signals in accordance therewith, said light detector being unaffected by shunted or coupled light from said light source;
a processing unit for processing said intensity signals received from said light detector through a signal analog path thereby producing output signals, said processing unit comprising:
first and second amplifiers for amplifying said intensity signals, each in accordance with a respective first and second gain amplification factor; and
a processor for automatically determining said first and second gain amplification factors in adjustable fashion;
wherein during a first stage, said first and second amplifiers amplify a DC signal component of said intensity signals in accordance with predetermined first and second gain amplification factors, said amplified DC signal component being subtracted from said intensity signals at an input of said first amplifier, to isolate an AC signal component of said intensity signals,
and wherein during a second stage, said second amplifier amplifies said isolated AC signal component in accordance with said adjustably-determined second gain amplification factor,
said processing unit producing output signals in accordance with said isolated AC signal component and said DC signal component and calculating in accordance therewith, at least one blood constituent level.

11. The device according to claim 10 wherein said processor develops a control signal when said adjustably-determined second gain amplification factor is established in said second stage, said control signal is able to shut off said light source.

12. The device according to claim 11 wherein said control signal conserves energy by reducing the operational duty cycle of said at least one light source.

13. The device according to claim 10 wherein said first and second gain amplification factors are determined by said processor in an iterative process by adjustably setting a gain amplification factor and measuring a dynamic voltage range of said output signals to determine if said voltage range falls within a predetermined window established by said processor.

14. A system comprising:
a non-invasive device for measurement of blood saturation and heart pulse rate, comprising:
a housing unit configured to be attachable to a head covering, said head covering disposed proximate to an organ being measured, said head covering comprising one of a group including a cap, a hat and a bandanna, said housing unit comprising:
at least one light source, providing light directed toward the surface of said organ, the light being reflected from said organ;
a light detector_spaced apart from said at least one light source and being sensitive to intensity levels of said reflected light for producing intensity signals in accordance therewith, said light detector being unaffected by shunted or coupled light from said light source;

a processing unit for processing said intensity signals received from said light detector through a signal analog path thereby producing output signals; and a transmitter configured to transmit said output signals to a receiver at a remote location; and a receiver configured to indicate an alert when the blood saturation or heart pulse rate falls outside of a predetermined range;

wherein said processing unit comprises mapping means for mapping the intensity of said AC signal component along the surface of said organ to detect regions of said organ having a reduced blood flow.

* * * * *